United States Patent
Emes et al.

(10) Patent No.: US 11,028,403 B2
(45) Date of Patent: Jun. 8, 2021

(54) METHODS OF INCREASING PLANT BIOMASS AND OILSEED PRODUCTION

(71) Applicant: University of Guelph, Guelph (CA)

(72) Inventors: Michael Emes, Guelph (CA); Ian Tetlow, Guelph (CA); Fushan Liu, Guelph (CA)

(73) Assignee: University of Guelph, Guelph (CA)

( * ) Notice: Subject to any disclaimer, the term of this patent is extended or adjusted under 35 U.S.C. 154(b) by 51 days.

(21) Appl. No.: 15/569,230

(22) PCT Filed: Apr. 28, 2016

(86) PCT No.: PCT/CA2016/050490
§ 371 (c)(1),
(2) Date: Oct. 25, 2017

(87) PCT Pub. No.: WO2016/172798
PCT Pub. Date: Nov. 3, 2016

(65) Prior Publication Data
US 2018/0312859 A1    Nov. 1, 2018

Related U.S. Application Data

(60) Provisional application No. 62/153,698, filed on Apr. 28, 2015.

(51) Int. Cl.
| | |
|---|---|
| C12N 15/82 | (2006.01) |
| C12P 7/64 | (2006.01) |
| C12N 9/10 | (2006.01) |
| C12P 19/00 | (2006.01) |
| C12N 15/52 | (2006.01) |

(52) U.S. Cl.
CPC ......... *C12N 15/8245* (2013.01); *C12N 9/107* (2013.01); *C12N 15/52* (2013.01); *C12N 15/8218* (2013.01); *C12N 15/8247* (2013.01); *C12N 15/8261* (2013.01); *C12P 7/64* (2013.01); *C12P 19/00* (2013.01); *Y02A 40/146* (2018.01)

(58) Field of Classification Search
None
See application file for complete search history.

(56) References Cited

U.S. PATENT DOCUMENTS 6,639,126 B1    10/2003 Sewalt et al.

FOREIGN PATENT DOCUMENTS

| WO | 0073422 A1 | 12/2000 |
|---|---|---|
| WO | 01/70942 A2 | 9/2001 |

OTHER PUBLICATIONS

Sequence Accession AAV29757, Apr. 16, 2009, attached at the end of the office action (Year: 2009).*
Kortstee et al., "Expression of *Escherichia coli* branching enzyme in tubers of amylose-free transgenic potato leads to an increased branching degree of the amylopectin", The Plant Journal, Blackwell Scientific Publications, Oxford, GB, vol. 10, No. 1, p. 83-90, Jan. 1, 1996.
Liu, Fushan et al., "Modification of starch metabolism in transgenic *Arabidopsis thaliana* increases plant biomass and riples oilseed production", Plant Biotechnology Journal, vol. 14, No. 3, p. 976-985, Mar. 1, 2016.
Makhmoudova, A. et al., "Identification of Multiple Phosphorylation Sites on Maize Endosperm Starch Branching Enzyme IIb, a Key Enzyme in Amylopectin Biosynthesis", Journal of Biological Chemistry, vol. 289, No. 13, p. 3233-9246, Mar. 28, 2014.
Tetlow, I.J. et al., "A review of starch-branching enzymes and their role in amylopectin biosynthesis: Starch-Branching Enzymes in Amylopectin Biosynthesis", IUBMB Life, vol. 66, No. 8, p. 546-558, Aug. 1, 2014.
Tanaka, N. et al., "The structure of starch can be manipulated by changing the expression levels of starch branching enzyme IIb in rice endosperm", Plant Biotechnology Journal, 2004, vol. 2, p. 507-516.
Jiang, H.Y. et al., "RNA interterence-mediated silencing of the starch branching enzyme gene improves", Genetics and Molecular Research, Jan. 2013, vol. 12, No. 3, pp. 2800-2808.
Carciofi, M. et al., "Concerted suppression of all starch branching enzyme genes in barley produces amylose-only starch granules", BMC Plant Biology 2012, vol. 12, No. 223, pp. 1471-2229.
Regina, A. et al., "High-amylose wheat generated by RNA interference improves indices of large-bowel health in rats", PNAS Mar. 2006, vol. 103, No. 10, pp. 3546-3551.
Regina, A. et al., "Control of starch branching in barley defined through differential RNAi suppression of starch branching enzyme IIa and IIb", Journal of Experimental Botany, Mar. 2010, vol. 61, No. 5, pp. 1469-1482.
Man J. et al., "Effect of simultaneous inhibition of starch branching enzymes I and IIb on the crystalline structure of rice starches with different amylose contents", J Agric Food Chem, Oct. 2013, vol. 61, No. 41, 9930-9937.

* cited by examiner

*Primary Examiner* — Elizabeth F McElwain
(74) *Attorney, Agent, or Firm* — Bereskin & Parr LLP/S.E.N.C.R.L., s.r.l.; Micheline Gravelle; Ainslie Parsons

(57) ABSTRACT

A novel method for increasing plant biomass and oilseed production is described. Transgenic plants with increased biomass and oilseed production are also described.

10 Claims, 10 Drawing Sheets

Specification includes a Sequence Listing.

(a) Oil production/plant (mg)

(b) Composition of fatty acids in seeds

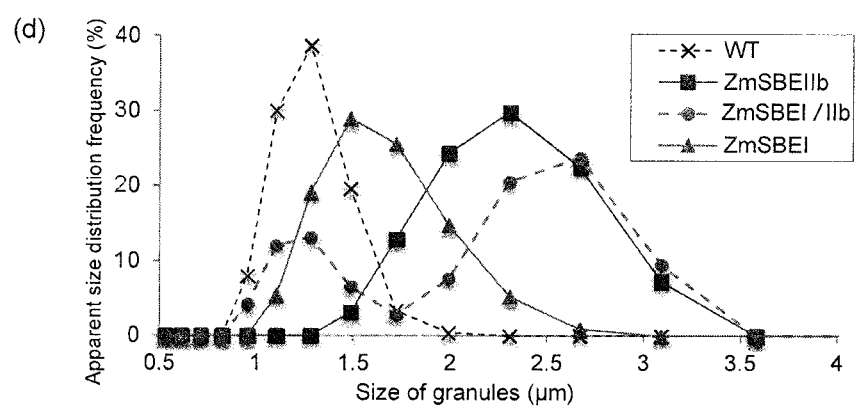
FIGURE 5 CON'T

CRISPR-A: to target two copies from genome A and C for BnSBE2.1

CRISPR-B: to target two copies from genome A and C for BnSBE2.2

CRISPR-C: to target BnSBE2.1 and BnSBE2.2 simultaneously

SEQUENCE LISTING

<160> NUMBER OF SEQ ID NOS: 28

<210> SEQ ID NO 1
<211> LENGTH: 2580

```
<212> TYPE: DNA
<213> ORGANISM: Zea mays

<400> SEQUENCE: 1
atgctgtgcc tcgtgtcgcc ctcttcctcg ccgactccgc ttccgccgcc gcggcgctct      60
cgctcgcatg ctgatcgggc ggcaccgccg gggatcgcgg gtggcggcaa tgtgcgcctg     120
agtgtgttgt ctgtccagtg caaggctcgc cggtcagggg tgcggaaggt caagagcaaa     180
ttcgccactg cagctactgt gcaagaagat aaaactatgg caactgccaa aggcgatgtc     240
gaccatctcc ccatatacga cctggacccc aagctggaga tattcaagga ccatttcagg     300
taccggatga aaagattcct agagcagaaa ggatcaattg aagaaaatga gggaagtctt     360 gaatctttt ctaaaggcta tttgaaattt gggattaata caaatgagga tggaactgta     420
tatcgtgaat gggcacctgc tgcgcaggag gcagagctta ttggtgactt caatgactgg     480
aatggtgcaa accataagat ggagaaggat aaatttggtg tttggtcgat caaaattgac     540
catgtcaaag gaaacctgc catccctcac aattccaagg ttaaatttcg ctttctacat     600
ggtggagtat gggttgatcg tattccagca ttgattcgtt atgcgactgt tgatgcctct     660
aaatttggag ctccctatga tggtgttcat tgggatcctc ctgcttctga aaggtacaca     720
tttaagcatc ctcggccttc aaagcctgct gctccacgta tctatgaagc ccatgtaggt     780
atgagtggtg aaaagccagc agtaagcaca tataggaat ttgcagacaa tgtgttgcca     840
cgcatacgag caaataacta caacacagtt cagttgatgg cagttatgga gcattcgtac     900
tatgcttctt tcgggtacca tgtgacaaat ttctttgcgg ttagcagcag atcaggcaca     960
ccagaggacc tcaaatatct tgttgataag gcacacagtt tgggtttgcg agttctgatg    1020
gatgttgtcc atagccatgc aagtaataat gtcacagatg gtttaaatgg ctatgatgtt    1080
ggacaaagca cccaagagtc ctattttcat gcgggagata gaggttatca taaactttgg    1140
gatagtcggc tgttcaacta tgctaactgg gaggtattaa ggtttcttct ttctaacctg    1200
agatattggt tggatgaatt catgtttgat ggcttccgat ttgatggagt tacatcaatg    1260
ctgtatcatc accatggtat caatgtgggg tttactggaa actaccagga atatttcagt    1320
ttggacacag ctgtggatgc agttgtttac atgatgcttg caaaccattt aatgcacaaa    1380
ctcttgccag aagcaactgt tgttgctgaa gatgtttcag gcatgccggt cctttgccgg    1440
ccagttgatg aaggtggggt tgggtttgac tatcgcctgg caatggctat ccctgataga    1500
tggattgact acctgaagaa taaagatgac tctgagtggt cgatgggtga aatagcgcat    1560
actttgacta caggagata tactgaaaaa tgcatcgcat atgctgagag ccatgatcag    1620
tctattgttg gcgacaaaac tattgcattt ctcctgatgg acaaggaaat gtacactggc    1680
atgtcagact gcagcctgc ttcacctaca attgatcgag ggattgcact ccaaaagatg    1740
attcacttca tcacaatggc cctggaggt gatggctact tgaattttat gggaaatgag    1800
tttggtcacc cagaatggat tgactttcca agagaaggga caactggag ctatgataaa    1860 tgcagacgac agtggagcct tgtggacact gatcacttgc ggtacaagta catgaatgcg    1920
tttgaccaag cgatgaatgc gctcgatgag agattttcct tcctttcgtc gtcaaagcag    1980
atcgtcagcg acatgaacga tgaggaaaag gttattgtct ttgaacgtgg agatttagtt    2040
tttgttttca atttccatcc caagaaaact tacgagggct acaaagtggg atgcgatttg    2100
cctgggaaat acagagtagc cctggactct gatgctctgg tcttcggtgg acatggaaga    2160
gttggccacg acgtggatca cttcacgtcg cctgaagggg tgccagggt gcccgaaacg    2220
```

```
aacttcaaca accggccgaa ctcgttcaaa gtcctttctc cgccccgcac ctgtgtggct    2280
tattaccgtg tagacgaagc aggggctgga cgacgtcttc acgcgaaagc agagacagga    2340
aagacgtctc cagcagagag catcgacgtc aaagcttcca gagctagtag caaagaagac    2400
aaggaggcaa cggctggtgg caagaaggga tggaagtttg cgcggcagcc atccgatcaa    2460
gataccaaat gaagccagga gtccttggtg aggactggac tggctgccgg cgccctgtta    2520
gtagtcctgc tctactggac tagccgccgc tggcgccctt ggaacggtcc tttcctgtag    2580
```

<210> SEQ ID NO 2
<211> LENGTH: 823
<212> TYPE: PRT
<213> ORGANISM: Zea mays

<400> SEQUENCE: 2

```
Met Leu Cys Leu Val Ser Pro Ser Ser Pro Thr Pro Leu Pro Pro
1               5                   10                  15

Pro Arg Arg Ser Arg Ser His Ala Asp Arg Ala Ala Pro Pro Gly Ile
            20                  25                  30

Ala Gly Gly Gly Asn Val Arg Leu Ser Val Leu Ser Val Gln Cys Lys
        35                  40                  45

Ala Arg Arg Ser Gly Val Arg Lys Val Lys Ser Lys Phe Ala Thr Ala
    50                  55                  60

Ala Thr Val Gln Glu Asp Lys Thr Met Ala Thr Ala Lys Gly Asp Val
65                  70                  75                  80

Asp His Leu Pro Ile Tyr Asp Leu Asp Pro Lys Leu Glu Ile Phe Lys
                85                  90                  95

Asp His Phe Arg Tyr Arg Met Lys Arg Phe Leu Glu Gln Lys Gly Ser
            100                 105                 110

Ile Glu Glu Asn Glu Gly Ser Leu Glu Ser Phe Ser Lys Gly Tyr Leu
        115                 120                 125

Lys Phe Gly Ile Asn Thr Asn Glu Asp Gly Thr Val Tyr Arg Glu Trp
    130                 135                 140

Ala Pro Ala Ala Gln Glu Ala Glu Leu Ile Gly Asp Phe Asn Asp Trp
145                 150                 155                 160

Asn Gly Ala Asn His Lys Met Glu Lys Asp Lys Phe Gly Val Trp Ser
                165                 170                 175

Ile Lys Ile Asp His Val Lys Gly Lys Pro Ala Ile Pro His Asn Ser
            180                 185                 190

Lys Val Lys Phe Arg Phe Leu His Gly Gly Val Trp Val Asp Arg Ile
        195                 200                 205

Pro Ala Leu Ile Arg Tyr Ala Thr Val Asp Ala Ser Lys Phe Gly Ala
    210                 215                 220

Pro Tyr Asp Gly Val His Trp Asp Pro Pro Ala Ser Glu Arg Tyr Thr
225                 230                 235                 240

Phe Lys His Pro Arg Pro Ser Lys Pro Ala Ala Pro Arg Ile Tyr Glu
                245                 250                 255

Ala His Val Gly Met Ser Gly Glu Lys Pro Ala Val Ser Thr Tyr Arg
            260                 265                 270

Glu Phe Ala Asp Asn Val Leu Pro Arg Ile Arg Ala Asn Asn Tyr Asn
        275                 280                 285

Thr Val Gln Leu Met Ala Val Met Glu His Ser Tyr Tyr Ala Ser Phe
    290                 295                 300

Gly Tyr His Val Thr Asn Phe Phe Ala Val Ser Ser Arg Ser Gly Thr
305                 310                 315                 320
```

```
Pro Glu Asp Leu Lys Tyr Leu Val Asp Lys Ala His Ser Leu Gly Leu
            325                 330                 335

Arg Val Leu Met Asp Val Val His Ser His Ala Ser Asn Asn Val Thr
            340                 345                 350

Asp Gly Leu Asn Gly Tyr Asp Val Gly Gln Ser Thr Gln Glu Ser Tyr
            355                 360                 365

Phe His Ala Gly Asp Arg Gly Tyr His Lys Leu Trp Asp Ser Arg Leu
            370                 375                 380

Phe Asn Tyr Ala Asn Trp Glu Val Leu Arg Phe Leu Ser Asn Leu
385                 390                 395                 400

Arg Tyr Trp Leu Asp Glu Phe Met Phe Asp Gly Phe Arg Phe Asp Gly
            405                 410                 415

Val Thr Ser Met Leu Tyr His His Gly Ile Asn Val Gly Phe Thr
            420                 425                 430

Gly Asn Tyr Gln Glu Tyr Phe Ser Leu Asp Thr Ala Val Asp Ala Val
            435                 440                 445

Val Tyr Met Met Leu Ala Asn His Leu Met His Lys Leu Leu Pro Glu
            450                 455                 460

Ala Thr Val Val Ala Glu Asp Val Ser Gly Met Pro Val Leu Cys Arg
465                 470                 475                 480

Pro Val Asp Glu Gly Gly Val Gly Phe Asp Tyr Arg Leu Ala Met Ala
            485                 490                 495

Ile Pro Asp Arg Trp Ile Asp Tyr Leu Lys Asn Lys Asp Asp Ser Glu
            500                 505                 510

Trp Ser Met Gly Glu Ile Ala His Thr Leu Thr Asn Arg Arg Tyr Thr
            515                 520                 525

Glu Lys Cys Ile Ala Tyr Ala Glu Ser His Asp Gln Ser Ile Val Gly
            530                 535                 540

Asp Lys Thr Ile Ala Phe Leu Leu Met Asp Lys Glu Met Tyr Thr Gly
545                 550                 555                 560

Met Ser Asp Leu Gln Pro Ala Ser Pro Thr Ile Asp Arg Gly Ile Ala
            565                 570                 575

Leu Gln Lys Met Ile His Phe Ile Thr Met Ala Leu Gly Gly Asp Gly
            580                 585                 590

Tyr Leu Asn Phe Met Gly Asn Glu Phe Gly His Pro Glu Trp Ile Asp
            595                 600                 605

Phe Pro Arg Glu Gly Asn Asn Trp Ser Tyr Asp Lys Cys Arg Arg Gln
            610                 615                 620

Trp Ser Leu Val Asp Thr Asp His Leu Arg Tyr Lys Tyr Met Asn Ala
625                 630                 635                 640

Phe Asp Gln Ala Met Asn Ala Leu Asp Glu Arg Phe Ser Phe Leu Ser
            645                 650                 655

Ser Ser Lys Gln Ile Val Ser Asp Met Asn Asp Glu Glu Lys Val Ile
            660                 665                 670

Val Phe Glu Arg Gly Asp Leu Val Phe Val Phe Asn Phe His Pro Lys
            675                 680                 685

Lys Thr Tyr Glu Gly Tyr Lys Val Gly Cys Asp Leu Pro Gly Lys Tyr
            690                 695                 700

Arg Val Ala Leu Asp Ser Asp Ala Leu Val Phe Gly His Gly Arg
705                 710                 715                 720

Val Gly His Asp Val Asp His Phe Thr Ser Pro Glu Gly Val Pro Gly
            725                 730                 735
```

```
Val Pro Glu Thr Asn Phe Asn Asn Arg Pro Asn Ser Phe Lys Val Leu
            740                 745                 750

Ser Pro Pro Arg Thr Cys Val Ala Tyr Tyr Arg Val Asp Glu Ala Gly
        755                 760                 765

Ala Gly Arg Arg Leu His Ala Lys Ala Glu Thr Gly Lys Thr Ser Pro
        770                 775                 780

Ala Glu Ser Ile Asp Val Lys Ala Ser Arg Ala Ser Ser Lys Glu Asp
785                 790                 795                 800

Lys Glu Ala Thr Ala Gly Gly Lys Lys Gly Trp Lys Phe Ala Arg Gln
                805                 810                 815

Pro Ser Asp Gln Asp Thr Lys
            820

<210> SEQ ID NO 3
<211> LENGTH: 2400
<212> TYPE: DNA
<213> ORGANISM: Zea mays

<400> SEQUENCE: 3
atggcgttcc gggtttctgg ggcggtgctc ggtggggccg taagggctcc ccgactcacc      60
ggcggcgggg agggtagtct agtcttccgg cacaccggcc tcttcttaac tcggggtgct     120
cgagttggat gttcggggac gcacggggcc atgcgcgcgg cggccgcggc caggaaggcg     180
gtcatggttc ctgagggcga gaatgatggc ctcgcatcaa gggctgactc ggctcaattc     240
cagtcggatg aactggaggt accagacatt tctgaagaga caacgtgcgg tgctggtgtg     300
gctgatgctc aagccttgaa cagagttcga gtggtccccc caccaagcga tggacaaaaa     360
atattccaga ttgaccccat gttgcaaggc tataagtacc atcttgagta cggtacagc      420
ctctatagaa gaatccgttc agacattgat gaacatgaag gaggcttgga agccttctcc     480
cgtagttatg agaagtttgg atttaatgcc agcgcggaag gtatcacata tcgagaatgg     540
gctcctggag cattttctgc agcattggtg ggtgacgtca acaactggga tccaaatgca     600
gatcgtatga gcaaaaatga gtttggtgtt tgggaaattt ttctgcctaa caatgcagat     660
ggtacatcac ctattcctca tggatctcgt gtaaaggtga aatggataca tccatcaggg     720
ataaaggatt caattccagc ctggatcaag tactcagtgc aggccccagg agaaatacca     780
tatgatggga tttattatga tcctcctgaa gaggtaaagt atgtgttcag gcatgcgcaa     840
cctaaacgac caaaatcatt gcggatatat gaaacacatg tcggaatgag tagcccggaa     900
ccgaagataa acacatatgt aaactttagg gatgaagtcc tcccaagaat aaaaaaactt     960
ggatacaatg cagtgcaaat aatggcaatc caagagcact catattatgg aagctttgga    1020
taccatgtaa ctaattttt tgcgccaagt agtcgttttg gtaccccaga agatttgaag    1080
tctttgattg atagagcaca tgagcttggt ttgctagttc tcatggatgt ggttcatagt    1140
catgcgtcaa gtaatactct ggatgggttg aatggttttg atggtacaga tacacattac    1200
tttcacagtg gtccacgtgg ccatcactgg atgtgggatt ctcgcctatt taactatggg    1260
aactgggaag ttttaagatt tcttctctcc aatgctagat ggtggctcga ggaatataag    1320
tttgatggtt ccgttttga tggtgtgacc tccatgatgt acactcacca cggattacaa    1380
gtaacattta cggggaactt caatgagtat tttggctttg ccaccgatgt agatgcagtg    1440
gtttacttga tgctggtaaa tgatctaatt catggacttt atcctgaggc tgtaaccatt    1500
ggtgaagatt ttagtggaat gcctacattt gcccttcctg ttcacgatgg tggggtaggt    1560
tttgactatc ggatgcatat ggctgtggct gacaaatgga ttgaccttct caagcaaagt    1620
```

```
gatgaaactt ggaagatggg tgatattgtg cacacactga caaataggag gtggttagag    1680
aagtgtgtaa cttatgctga aagtcatgat caagcattag tcggcgacaa gactattgcg    1740
ttttggttga tggacaagga tatgtatgat ttcatggccc tcgatagacc ttcaactcct    1800
accattgatc gtgggatagc attacataag atgattagac ttatcacaat gggtttagga    1860
ggagagggct atcttaattt catgggaaat gagtttggac atcctgaatg gatagatttt    1920
ccaagaggtc cgcaaagact tccaagtggt aagtttattc cagggaataa caacagttat    1980
gacaaatgtc gtcgaagatt tgacctgggt gatgcagact atcttaggta tcatggtatg    2040
caagagtttg atcaggcaat gcaacatctt gagcaaaaat atgaattcat gacatctgat    2100
caccagtata tttcccggaa acatgaggag gataaggtga ttgtgttcga aagggagat    2160 ttggtatttg tgttcaactt ccactgcaac aacagctatt ttgactaccg tattggttgt    2220
cgaaagcctg gggtgtataa ggtggtcttg gactccgacg ctggactatt tggtggattt    2280
agcaggatcc atcacgcagc cgagcacttc accgccgact gttcgcatga taataggcca    2340
tattcattct cggtttatac accaagcaga acatgtgtcg tctatgctcc agtggagtga    2400
```

<210> SEQ ID NO 4
<211> LENGTH: 799
<212> TYPE: PRT
<213> ORGANISM: Zea mays

<400> SEQUENCE: 4

```
Met Ala Phe Arg Val Ser Gly Ala Val Leu Gly Gly Ala Val Arg Ala
1               5                   10                  15

Pro Arg Leu Thr Gly Gly Glu Gly Ser Leu Val Phe Arg His Thr
            20                  25                  30

Gly Leu Phe Leu Thr Arg Gly Ala Arg Val Gly Cys Ser Gly Thr His
        35                  40                  45

Gly Ala Met Arg Ala Ala Ala Ala Arg Lys Ala Val Met Val Pro
    50                  55                  60

Glu Gly Glu Asn Asp Gly Leu Ala Ser Arg Ala Asp Ser Ala Gln Phe
65                  70                  75                  80

Gln Ser Asp Glu Leu Glu Val Pro Asp Ile Ser Glu Glu Thr Thr Cys
                85                  90                  95

Gly Ala Gly Val Ala Asp Ala Gln Ala Leu Asn Arg Val Arg Val Val
            100                 105                 110

Pro Pro Pro Ser Asp Gly Gln Lys Ile Phe Gln Ile Asp Pro Met Leu
        115                 120                 125

Gln Gly Tyr Lys Tyr His Leu Glu Tyr Arg Tyr Ser Leu Tyr Arg Arg
    130                 135                 140

Ile Arg Ser Asp Ile Asp Glu His Glu Gly Gly Leu Glu Ala Phe Ser
145                 150                 155                 160

Arg Ser Tyr Glu Lys Phe Gly Phe Asn Arg Ser Ala Glu Gly Ile Thr
                165                 170                 175

Tyr Arg Glu Trp Ala Pro Gly Ala Phe Ser Ala Ala Leu Val Gly Asp
            180                 185                 190

Phe Asn Asn Trp Asp Pro Asn Ala Asp Arg Met Ser Lys Asn Glu Phe
        195                 200                 205

Gly Val Trp Glu Ile Phe Leu Pro Asn Asn Ala Asp Gly Thr Ser Pro
    210                 215                 220

Ile Pro His Gly Ser Arg Val Lys Val Arg Met Asp Thr Pro Ser Gly
225                 230                 235                 240
```

```
Ile Lys Asp Ser Ile Pro Ala Trp Ile Lys Tyr Ser Val Gln Ala Pro
                245                 250                 255

Gly Glu Ile Pro Tyr Asp Gly Ile Tyr Tyr Asp Pro Pro Glu Glu Val
                260                 265                 270

Lys Tyr Val Phe Arg His Ala Gln Pro Lys Arg Pro Lys Ser Leu Arg
                275                 280                 285

Ile Tyr Glu Thr His Val Gly Met Ser Ser Pro Glu Pro Lys Ile Asn
                290                 295                 300

Thr Tyr Val Asn Phe Arg Asp Glu Val Leu Pro Arg Ile Lys Lys Leu
305                 310                 315                 320

Gly Tyr Asn Ala Val Gln Ile Met Ala Ile Gln Glu His Ser Tyr Tyr
                325                 330                 335

Gly Ser Phe Gly Tyr His Val Thr Asn Phe Ala Pro Ser Ser Arg
                340                 345                 350

Phe Gly Thr Pro Glu Glu Leu Lys Ser Leu Ile Asp Arg Ala His Glu
                355                 360                 365

Leu Gly Leu Leu Val Leu Met Asp Val Val His Ser His Ala Ser Ser
                370                 375                 380

Asn Thr Leu Asp Gly Leu Asn Gly Phe Asp Gly Thr Asp Thr His Tyr
385                 390                 395                 400

Phe His Ser Gly Pro Arg Gly His His Trp Met Trp Asp Ser Arg Leu
                405                 410                 415

Phe Asn Tyr Gly Asn Trp Glu Val Leu Arg Phe Leu Leu Ser Asn Ala
                420                 425                 430

Arg Trp Trp Leu Glu Glu Tyr Lys Phe Asp Gly Phe Arg Phe Asp Gly
                435                 440                 445

Val Thr Ser Met Met Tyr Thr His His Gly Leu Gln Val Thr Phe Thr
                450                 455                 460

Gly Asn Phe Asn Glu Tyr Phe Gly Phe Ala Thr Asp Val Asp Ala Val
465                 470                 475                 480

Val Tyr Leu Met Leu Val Asn Asp Leu Ile His Gly Leu Tyr Pro Glu
                485                 490                 495

Ala Val Thr Ile Gly Glu Asp Val Ser Gly Met Pro Thr Phe Ala Leu
                500                 505                 510

Pro Val His Asp Gly Gly Val Gly Phe Asp Tyr Arg Met His Met Ala
                515                 520                 525

Val Ala Asp Lys Trp Ile Asp Leu Leu Lys Gln Ser Asp Glu Thr Trp
                530                 535                 540

Lys Met Gly Asp Ile Val His Thr Leu Thr Asn Arg Arg Trp Leu Glu
545                 550                 555                 560

Lys Cys Val Thr Tyr Ala Glu Ser His Asp Gln Ala Leu Val Gly Asp
                565                 570                 575

Lys Thr Ile Ala Phe Trp Leu Met Asp Lys Asp Met Tyr Asp Phe Met
                580                 585                 590

Ala Leu Asp Arg Pro Ser Thr Pro Thr Ile Asp Arg Gly Ile Ala Leu
                595                 600                 605

His Lys Met Ile Arg Leu Ile Thr Met Gly Leu Gly Gly Glu Gly Tyr
                610                 615                 620

Leu Asn Phe Met Gly Asn Glu Phe Gly His Pro Glu Trp Ile Asp Phe
625                 630                 635                 640

Pro Arg Gly Pro Gln Arg Leu Pro Ser Gly Lys Phe Ile Pro Gly Asn
                645                 650                 655
```

-continued

Asn Asn Ser Tyr Asp Lys Cys Arg Arg Phe Asp Leu Gly Asp Ala
            660                 665                 670

Asp Tyr Leu Arg Tyr His Gly Met Gln Glu Phe Asp Gln Ala Met Gln
        675                 680                 685

His Leu Glu Gln Lys Tyr Glu Phe Met Thr Ser Asp His Gln Tyr Ile
    690                 695                 700

Ser Arg Lys His Glu Glu Asp Lys Val Ile Val Phe Glu Lys Gly Asp
705                 710                 715                 720

Leu Val Phe Val Phe Asn Phe His Cys Asn Asn Ser Tyr Phe Asp Tyr
                725                 730                 735

Arg Ile Gly Cys Arg Lys Pro Gly Val Tyr Lys Val Val Leu Asp Ser
            740                 745                 750

Asp Ala Gly Leu Phe Gly Gly Phe Ser Arg Ile His His Ala Ala Glu
        755                 760                 765

His Phe Thr Ala Asp Cys Ser His Asp Asn Arg Pro Tyr Ser Phe Ser
    770                 775                 780

Val Tyr Thr Pro Ser Arg Thr Cys Val Val Tyr Ala Pro Val Glu
785                 790                 795

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tcgggatact gtctctgacg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tctctgtttc ctgggcttct                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tctcgacctc tcaacactgg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aaactccgca gattgtttcc                                              20

<210> SEQ ID NO 9
<211> LENGTH: 20
<212> TYPE: DNA

```
<213> ORGANISM: Artificial Sequence
<220> FEATURE:
<223> OTHER INFORMATION: Synthetic

<400> SEQUENCE: 9
gggaccactc gaactctgtt                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctcaattcca gtcggatgaa                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
aagaagacaa ggaggcaacg                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ggtatcttga tcggatggct                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gccgatgctg atgacattca                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ctccagcgaa tccagcctta                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gcatcaaaga acacactgga                                                  20
```

-continued

```
<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gggaattaca acgagtactt                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gatcgtcgtt gaaacttggg                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gtatttccac tctggatcgc                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ggatggcata gtgataaccg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gattcttctg taacgttgct                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gacgacccta ctcgaattaa                                                    20

<210> SEQ ID NO 22
<211> LENGTH: 20
<212> TYPE: DNA
<213> ORGANISM: Artificial Sequence
<220> FEATURE:
```

<223> OTHER INFORMATION: Synthetic

<400> SEQUENCE: 22
gtctttgtaa ctctgcaaca                                                    20

<210> SEQ ID NO 23
<211> LENGTH: 2526
<212> TYPE: DNA
<213> ORGANISM: Artificial Sequence
<220> FEATURE:
<223> OTHER INFORMATION: Synthetic

<400> SEQUENCE: 23

| | | | | | |
|---|---|---|---|---|---|
| cgacttgcct | tccgcacaat | acatcatttc | ttcttagctt | ttttcttct | tcttcgttca | 60 |
| tacagttttt | ttttgtttat | cagcttacat | tttcttgaac | cgtagctttc | gttttcttct | 120 |
| ttttaacttt | ccattcggag | tttttgtatc | ttgtttcata | gtttgtccca | ggattagaat | 180 |
| gattaggcat | cgaaccttca | agaatttgat | tgaataaaac | atcttcattc | ttaagatatg | 240 |
| aagataatct | tcaaaaggcc | cctgggaatc | tgaaagaaga | gaagcaggcc | catttatatg | 300 |
| ggaaagaaca | atagtatttc | ttatataggc | ccatttaagt | tgaaaacaat | cttcaaaagt | 360 |
| cccacatcgc | ttagataaga | aaacgaagct | gagtttatat | acagctagag | tcgaagtagt | 420 |
| gattgcatca | agaacacac | tggagtttta | gagctagaaa | tagcaagtta | aaataaggct | 480 |
| agtccgttat | caacttgaaa | aagtggcacc | gagtcggtgc | ttttttttgc | aaaattttcc | 540 |
| agatcgattt | cttcttcctc | tgttcttcgg | cgttcaattt | ctgggttttt | ctcttcgttt | 600 |
| tctgtaactg | aaacctaaaa | tttgacctaa | aaaaatctc | aaataatatg | attcagtggt | 660 |
| tttgtacttt | tcagttagtt | gagttttgca | gttccgatga | gataaaccaa | tattaatcca | 720 |
| aactactgca | gcctgacaga | caaatgagga | tgcaaacaat | tttaaagttt | atctaacgct | 780 |
| agctgttttg | tttcttctct | ctggtgcacc | aacgacggcg | ttttctcaat | cataaagagg | 840 |
| cttgttttac | ttaaggccaa | taatgttgat | ggatcgaaag | aagagggctt | taataaacg | 900 |
| agcccgttta | agctgtaaac | gatgtcaaaa | acatcccaca | tcgttcagtt | gaaaatagaa | 960 |
| gctctgttta | tatattggta | gagtcgacta | agagattgac | gaccctactc | gaattaagtt | 1020 |
| ttagagctag | aaatagcaag | ttaaaataag | gctagtccgt | tatcaacttg | aaaaagtggc | 1080 |
| accgagtcgg | tgcttttttt | ggatagaatt | tcccagcttt | tttgcgtgtt | tcagctctca | 1140 |
| tgatccttgg | ccaatgggtg | tagtaaattt | tctgcacatt | cattggatgg | aaaataatgg | 1200 |
| ttttagcttt | agggaataag | aaaagtgtat | aggaagggga | ttttgtaca | atcacatttg | 1260 |
| aattaggtct | ttgaaatgac | agggaatgag | gacatatgat | gagacggtca | ttgttttagt | 1320 |
| tccaccacga | ttatatttga | aatttacgtg | agtgtgagtg | agacttgcat | aagaaaataa | 1380 |
| aatctttagt | tgggaaaaaa | ttcaataata | taaatgggct | tgagaaggaa | gcgagggata | 1440 |
| ggcctttttc | taaataggc | ccatttaagc | tattaacaat | cttcaaaagt | accacagcgc | 1500 |
| ttaggtaaag | aaagcagctg | agtttatata | tggttagaga | cgaagtagtg | attgatcgtc | 1560 |
| gttgaaactt | ggggttttag | agctagaaat | agcaagttaa | aataaggcta | gtccgttatc | 1620 |
| aacttgaaaa | agtggcaccg | agtcggtgct | ttttttggc | aaaaattttc | agatttttc | 1680 |
| ttcatctgta | gatttctggg | ttttttttc | cgtttcgtga | atcataagtg | aagttttgga | 1740 |
| tgcaaatctg | cgcgaaaaaa | gttggacctg | caatgagctt | atttagatag | ctaagacaaa | 1800 |
| gtgattggtc | cgttcgactt | gccttccgca | caatacatca | tttcttctta | gcttttttc | 1860 |
| ttcttcttcg | ttcatacagt | ttttttttgt | ttatcagctt | acatttttctt | gaaccgtagc | 1920 |

```
tttcgttttc ttcttttaa ctttccattc ggagttttg tatcttgttt catagtttgt      1980
cccaggatta gaatgattag gcatcgaacc ttcaagaatt tgattgaata aaacatcttc      2040
attcttaaga tatgaagata atcttcaaaa ggccctggg aatctgaaag aagagaagca      2100
ggcccattta tatgggaaag aacaatagta tttcttatat aggcccattt aagttgaaaa      2160
caatcttcaa aagtcccaca tcgcttagat aagaaaacga agctgagttt atatacagct      2220
agagtcgaag tagtgattgt atttccactc tggatcgcgt tttagagcta gaaatagcaa      2280
gttaaaataa ggctagtccg ttatcaactt gaaaaagtgg caccgagtcg gtgctttttt      2340
ttgcaaaatt ttccagatcg atttcttctt cctctgttct tcggcgttca atttctgggg      2400
ttttctcttc gttttctgta actgaaacct aaaatttgac ctaaaaaaaa tctcaaataa      2460
tatgattcag tggttttgta cttttcagtt agttgagttt tgcagttccg atgagataaa      2520
ccaata                                                                2526

<210> SEQ ID NO 24
<211> LENGTH: 2526
<212> TYPE: DNA
<213> ORGANISM: Artificial Sequence
<220> FEATURE:
<223> OTHER INFORMATION: Synthetic

<400> SEQUENCE: 24
cgacttgcct tccgcacaat acatcatttc ttcttagctt ttttcttct tcttcgttca        60 tacagttttt ttttgtttat cagcttacat tttcttgaac cgtagctttc gttttcttct      120
ttttaacttt ccattcggag ttttgtatc ttgtttcata gtttgtccca ggattagaat       180
gattaggcat cgaaccttca agaatttgat tgaataaaac atcttcattc ttaagatatg      240
aagataatct tcaaaaggcc cctgggaatc tgaaagaaga gaagcaggcc catttatatg      300
ggaaagaaca atagtatttc ttatataggc ccatttaagt tgaaaacaat cttcaaaagt      360
cccacatcgc ttagataaga aaacgaagct gagtttatat acagctagag tcgaagtagt      420
gattggatgg catagtgata accggtttta gagctagaaa tagcaagtta aaataaggct      480
agtccgttat caacttgaaa aagtggcacc gagtcggtgc ttttttttgc aaaattttcc      540
agatcgattt cttcttcctc tgttcttcgg cgttcaattt ctggggtttt ctcttcgttt      600
tctgtaactg aaacctaaaa tttgacctaa aaaaatctc aataatatg attcagtggt       660 tttgtacttt tcagttagtt gagttttgca gttccgatga gataaaccaa tattaatcca      720
aactactgca gcctgacaga caaatgagga tgcaaacaat tttaaagttt atctaacgct      780
agctgttttg tttcttctct ctggtgcacc aacgacggcg ttttctcaat cataagagg       840 cttgttttac ttaaggccaa taatgttgat ggatcgaaaa agagggctt ttaataaacg       900 agcccgttta agctgtaaac gatgtcaaaa acatcccaca tcgttcagtt gaaaatagaa      960
gctctgttta tatattggta gagtcgacta agagatttta attcgagtag gtcgtcgtt      1020 ttagagctag aaatagcaag ttaaaataag gctagtccgt tatcaacttg aaaaagtggc     1080
accgagtcgg tgcttttttt ggatagaatt tcccagcttt tttgcgtgtt tcagctctca     1140
tgatccttgg ccaatgggtg tagtaaattt tctgcacatt cattgatgg aaaataatgg      1200 ttttagcttt agggaataag aaaagtgtat aggaagggga tttttgtaca atcacatttg     1260
aattaggtct ttgaaatgac agggaatgag gacatatgat gagacggtca ttgttttagt     1320
tccaccacga ttatatttga aatttacgtg agtgtgagtg agacttgcat aagaaaataa     1380
```

```
aatctttagt tgggaaaaaa ttcaataata taaatgggct tgagaaggaa gcgagggata    1440 ggccttttc taaaataggc ccatttaagc tattaacaat cttcaaaagt accacagcgc    1500
ttaggtaaag aaagcagctg agtttatata tggttagaga cgaagtagtg attgattctt    1560
ctgtaacgtt gctgttttag agctagaaat agcaagttaa ataaggcta gtccgttatc    1620 aacttgaaaa agtggcaccg agtcggtgct ttttttggc aaaaattttc agattttttc    1680
ttcatctgta gatttctggg tttttttttc cgtttcgtga atcataagtg aagttttgga    1740
tgcaaatctg cgcgaaaaaa gttggacctg caatgagctt atttagatag ctaagacaaa    1800
gtgattggtc cgttcgactt gccttccgca caatacatca tttcttctta gcttttttc    1860 ttcttcttcg ttcatacagt tttttttgt ttatcagctt acattttctt gaaccgtagc    1920 tttcgtttc ttcttttaa ctttccattc ggagttttg tatcttgttt catagtttgt    1980
cccaggatta gaatgattag gcatcgaacc ttcaagaatt tgattgaata aaacatcttc    2040
attcttaaga tatgaagata atcttcaaaa ggccctggg aatctgaaag aagagaagca    2100
ggcccattta tatgggaaag aacaatagta tttcttatat aggcccattt aagttgaaaa    2160
caatcttcaa aagtcccaca tcgcttagat aagaaaacga agctgagttt atatacagct    2220
agagtcgaag tagtgattgt ctttgtaact ctgcaacagt tttagagcta gaaatagcaa    2280
gttaaaataa ggctagtccg ttatcaactt gaaaagtgg caccgagtcg gtgctttttt    2340
ttgcaaaatt ttccagatcg atttcttctt cctctgttct tcggcgttca atttctgggg    2400
ttttctcttc gttttctgta actgaaacct aaaatttgac ctaaaaaaaa tctcaaataa    2460
tatgattcag tggttttgta cttttcagtt agttgagttt tgcagttccg atgagataaa    2520
ccaata                                                                2526
```

<210> SEQ ID NO 25  
<211> LENGTH: 20  
<212> TYPE: DNA  
<213> ORGANISM: Artificial Sequence  
<220> FEATURE:  
<223> OTHER INFORMATION: Synthetic
<400> SEQUENCE: 25
gatcgtcgtt gaaacttggg             20

<210> SEQ ID NO 26  
<211> LENGTH: 20  
<212> TYPE: DNA  
<213> ORGANISM: Artificial Sequence  
<220> FEATURE:  
<223> OTHER INFORMATION: Synthetic
<400> SEQUENCE: 26
gagagagaag gagacggcgt             20

<210> SEQ ID NO 27  
<211> LENGTH: 20  
<212> TYPE: DNA  
<213> ORGANISM: Artificial Sequence  
<220> FEATURE:  
<223> OTHER INFORMATION: Synthetic
<400> SEQUENCE: 27
gtgtagggaa gatcttcgct             20

<210> SEQ ID NO 28  
<211> LENGTH: 20

```
<212> TYPE: DNA
<213> ORGANISM: Artificial Sequence
<220> FEATURE:
<223> OTHER INFORMATION: Synthetic

<400> SEQUENCE: 28
gcaccatcat caacattatc                                              20
```

//]: #

METHODS OF INCREASING PLANT BIOMASS AND OILSEED PRODUCTION

This application is a national phase entry application of Patent Cooperation Treaty Application No. PCT/CA2016/050490 (which designated the U.S.), which claims the benefit under 35 USC § 119 (e) from US provisional application Ser. No. 62/153,698, filed Apr. 28, 2015, both of which are incorporated by reference herein in their entirety.

INCORPORATION OF SEQUENCE LISTING

A computer readable form of the Sequence Listing "6580-P47431US02_SequenceListing.txt" (32,768 bytes), submitted via EFS-WEB and created on Oct. 24, 2017, is herein incorporated by reference.

FIELD

The present disclosure relates to novel methods for increasing plant biomass and oilseed production. The disclosure also relates to transgenic plants with increased biomass and oilseed production.

BACKGROUND

There are currently unprecedented pressures on global food and fuel supplies due to an increasing world population (estimated to be 9.6 billion by 2050) and, at the same time, loss of agricultural land to urban growth as well as climate change. In particular, enhanced affluence in many emerging world economies exacerbates these problems as meat consumption and automobile ownership increase, placing extra demands on crop yields to meet requests for livestock production and biofuels for fossil fuel replacements. Human civilization is reliant on a surprisingly narrow range of crops to supply its basic caloric requirements; broadly, these are starch storing cereals and lipid-storing crop seeds. In addition to their prominent role in the human food chain, cereal starches and oilseed derived lipids (triacylglycerols; TAG) are increasingly employed as fossil fuel supplements. When used as starting material for synthesis of bioethanol and biodiesel, respectively, they act as an 8-10-year stop-gap prior to the predicted advent of economically viable cellulosic ethanol[1-3]. Based on current population growth, food production must also increase 50% by 2030, and double by 2050 in order to meet projected demands[4]. It is therefore imperative to produce higher biomass and/or higher yielding crops to ensure both greater food and energy security.

Several strategies are currently being used that aim at yield and biomass increases in crop plants. In principle, they can be divided into three main groups but in some cases two strategies are combined.

First, increasing rates of photosynthesis (and/or reducing photorespiration) is expected to result in higher plant productivity, which ultimately relies on photosynthetic $CO_2$ fixation though, to date, this strategy has produced relatively small gains[5-8].

Second, seed yield can be increased by modulating flower induction and/or seed production, e.g. by preventing seed abortion as affected by environmental factors or intermediary carbon metabolism[9-12].

Third, the yield of a distinct plant product can be enhanced by taking advantage of knowledge of biosynthetic routes or of carbon partitioning within a plant organ.

Recent gains in enhancing oilseed TAG content have involved multiple approaches: for example, the manipulation of transcriptional master regulators such as WRINKLED1 (WRI1) to drive glycolysis and fatty acid (FA) synthesis[13, 14], over-expression of diacylglycerolacyltransferase (DGAT1) to create a sink for TAG[15], or reducing turnover by inhibition of lypolytic reactions[16-19]. These three approaches have been termed "push" (increasing FA synthesis), "pull" (enhancing TAG assembly) and "accumulation" (increasing TAG storage or reducing breakdown). Currently, attempts at stacking these gene modifications in the model plant *Arabidopsis thaliana* (*Arabidopsis*) have produced synergistic relationships, in some cases boosting TAG yield by 15 to 20%[19-21].

Efforts to enhance cereal yield through manipulation of biosynthetic and/or partitioning pathways have followed similar approaches, largely focused on increasing the direct precursors of the various end products[22-24], or increasing sink capacity via increasing demand, and have met with limited successes[15, 25]. For example, starch accumulation has been manipulated by altering the first committed enzyme of the biosynthetic path, ADPglucose pyrophosphorylase (AGPase) which forms the common glucosyl donor used by all higher plant starch synthases. Typically, the enzyme is highly sensitive to both allosteric modulation and redox regulation[26]. Manipulation of AGPase expression resulted in variable yield increases in different crops[22, 27-30] but also in unexpected results suggesting more complex control mechanisms[26, 27]. In the case of cereals, yield increases were, surprisingly, due to enhanced seed number and survival of the seeds rather than to increased starch per seed[28-30].

A need remains for new methods to increase crop yields.

SUMMARY

The inventors have developed a novel approach for increasing biomass and oil production in oilseed plants through the replacement of two endogenous leaf starch branching enzymes (SBEs) with cereal endosperm-specific isoforms.

Accordingly, one aspect of the disclosure provides a method of increasing the biomass, seed production and/or oil production of a plant cell, plant or plant part comprising:

(a) transforming the plant cell, plant or plant part with a nucleic acid molecule encoding an exogenous starch-branching enzyme, and (b) expressing the transformed nucleic acid molecule in the plant cell, plant or plant part.

In one embodiment, the plant cell, plant or plant part has reduced activity or expression or no activity or expression of at least one endogenous starch-branching enzyme.

In another embodiment, the transformed plant cell, plant or plant part has increased biomass, seed production and/or oil production compared to a wild-type plant cell, plant or plant part.

In another embodiment, the nucleic acid molecule is expressed in the plant cell, plant or plant part in an amount effective to increase biomass, seed production and/or oil production of the plant cell, plant or plant part.

In another embodiment, the nucleic acid molecule is from a cereal plant, optionally maize, wheat, barley, sorghum, oat, rye, millet, triticale or rice.

In another embodiment, the plant cell, plant or plant part is an oilseed crop, optionally canola, camelina, cotton, flaxseed, mustard, rapeseed, soybean, sunflower seed or palm.

In another embodiment, the plant cell, plant or plant part is a dicotyledon.

In another embodiment, the nucleic acid molecule comprises a nucleic acid sequence that has at least 80% sequence identity with a nucleic acid sequence selected from SEQ ID NO: 1 or 3.

In another embodiment, the method comprises transforming the plant cell, plant or plant part with a first nucleic acid molecule and a second nucleic acid molecule, each encoding an exogenous starch-branching enzyme.

In another embodiment, the first nucleic acid molecule comprises a nucleic acid sequence that has at least 80% sequence identity with SEQ ID NO: 1, and the second nucleic acid molecule comprises a nucleic acid sequence that has at least 80% sequence identity with SEQ ID NO: 3.

The disclosure also provides a transgenic plant produced using the methods described above. The disclosure further provides a seed of the plant and a plant cell of the plant.

Another aspect of the disclosure provides a transformed plant cell, plant or plant part expressing at least one nucleic acid molecule encoding an exogenous starch-branching enzyme, wherein said transformed plant cell, plant or plant part has increased biomass, seed production and/or oil production compared to a wild-type plant cell, plant or plant part.

In one embodiment, the plant cell, plant or plant part has reduced activity or expression or no activity or expression of at least one endogenous starch-branching enzyme.

In another embodiment, the nucleic acid molecule is from a cereal plant, optionally maize, wheat, barley, sorghum, oat, rye, millet, triticale or rice.

In another embodiment, the plant cell, plant or plant part is an oil-seed crop, optionally canola, camelina, cotton, flaxseed, mustard, rapeseed, soybean, sunflower seed or palm.

In another embodiment, the plant cell, plant or plant part is a dicotyledon.

In another embodiment, the nucleic acid molecule comprises a nucleic acid sequence that has at least 80% sequence identity with a nucleic acid sequence selected from SEQ ID NO: 1 or 3.

In another embodiment, the transformed plant cell, plant or plant part expresses a first nucleic acid molecule encoding a first exogenous starch-branching enzyme and a second nucleic acid molecule encoding a second exogenous starch-branching enzyme.

Optionally, the first nucleic acid molecule comprises a nucleic acid sequence that has at least 80% sequence identity with SEQ ID NO: 1, and the second nucleic acid molecule comprises a nucleic acid sequence that has at least 80% sequence identity with SEQ ID NO: 3.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

Amyloplast preparations from maize (Zea mays) were used as a positive control for detection with the anti-maize SBEI antibody.

Figure 9:
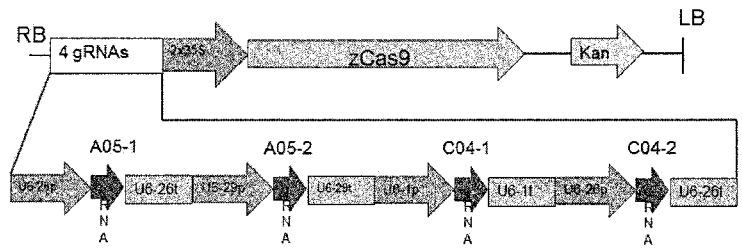
Figure 9:
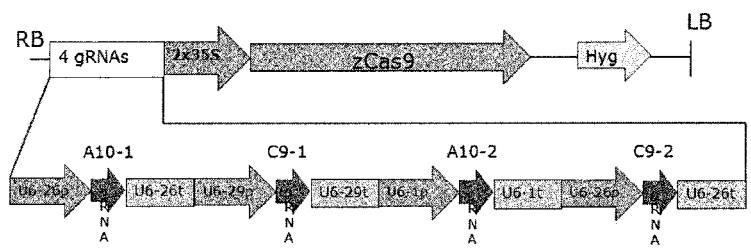
Figure 9:
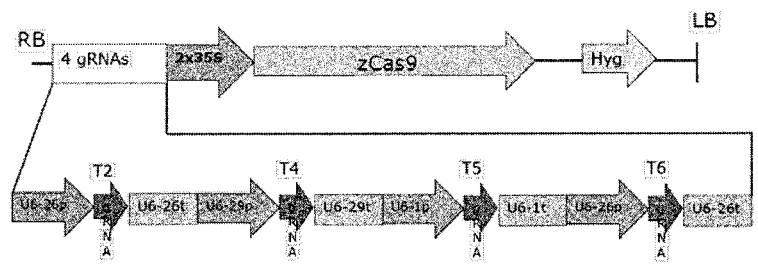

FIG. 9 shows a schematic illustration of three CRISPR constructs. CRISPR-A targets two copies from chromosome A and C for BnSBE2.1, CRISPR-B targets two copies from chromosome A and C for BnSBE2.2 and CRISPR-C targets BnSBE2.1 and BnSBE2.2 simultaneously.

DETAILED DESCRIPTION

I. Definitions

As used herein, the term "transformation" refers to a process for introducing exogenous nucleic acids into a plant cell, plant, or plant part. The terms "transformed," "transgenic," and "recombinant" refer to a host organism such as a plant cell, plant, or plant part into which an exogenous nucleic acid molecule has been introduced. The nucleic acid molecule can be stably integrated into the genome of the host or the nucleic acid molecule can be present as an extrachromosomal molecule. Transformed plant cells, plants, or plant parts are understood to encompass not only the end product of a transformation process, but also transgenic progeny thereof. A "non-transformed," "non-transgenic," or "non-recombinant" host refers to a wild-type organism, e.g., a plant cell, plant, or plant part which does not contain the exogenous nucleic acid molecule.

The term "plant" as used herein includes whole plants, progeny of the plants and plant parts, including seeds, siliques, fruit, leaves, flowers, shoots, stems, roots, isolated plant cells, tissues and organs.

The term "plant cell" as used herein includes plant cells which are derived and/or isolated from plant cell tissue or plant cell culture.

As used herein, the term "plant part" includes any part or parts of a plant including the seeds, siliques, fruit, leaves, flowers, shoots, stems and/or roots.

The term "exogenous" when used herein to refer to a nucleic acid molecule (for example, a DNA sequence), gene or protein, that originates from a source foreign to the particular plant cell, plant, or plant part into which it is introduced. The exogenous nucleic acid molecule may be introduced into the plant in a stable or transient manner, so as to produce a RNA molecule and/or a polypeptide molecule.

An "endogenous" nucleic acid molecule, gene or protein is a nucleic acid molecule (for example, a DNA sequence), gene or protein naturally associated with, or native to, a particular plant cell, plant, or plant part.

The term "nucleic acid molecule" or "nucleic acid sequence" as used herein refers to deoxyribonucleotides or ribonucleotides and polymers thereof in either single- or double-stranded form. The terms "nucleic acid molecule" or "nucleic acid sequence" may also be used interchangeably with gene, cDNA, and mRNA encoded by a gene. The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "biomass", "biomass of a plant" or "plant biomass" as used herein refers to the amount of a tissue produced by a plant. An increase in plant biomass can be in the whole plant or in parts thereof such as above-ground (harvestable) parts, seeds, siliques, fruit, leaves, flowers, shoots, stems and/or roots. Plant biomass can be measured, for example, by fresh weight and/or dry weight.

The term "increasing biomass" as used herein means that the plant or parts thereof have increased in size, height and/or mass as compared to a native or wild-type plant (i.e. a plant not transformed with the exogenous nucleic acid molecules described herein) or as compared to a predetermined standard.

The term "increasing seed production" as used herein refers to increasing the number of seeds per plant, the number of siliques per plant, the number of flowers per plant and/or the number of seeds per silique as compared to a native or wild-type plant or as compared to a predetermined standard. The term also refers to increasing seed size and/or seed length as compared to a native or wild-type plant or as compared to a predetermined standard.

The term "increasing oil production" as used herein refers to increasing the oil content of a plant, the oil content of the seeds of a plant and/or the oil content per seed as compared to a native or wild-type plant or as compared to a predetermined standard. The term "increasing oil production" also refers to increasing the seed yield (for example, number of seeds per plant, seed weight per plant, number of siliques per plant, number of flowers per plant, and/or seed size) as compared to a native or wild-type plant or as compared to a predetermined standard.

The term "increasing" or "improving" as used herein refers to at least a 2%, 5%, 10%, 25%, 50%, 100%, 200%, 300%, 400% or 500% increase in biomass, seed production and/or oil production compared to a native or wild-type plant or a predetermined standard.

The term "sequence identity" or "percent identity" as used herein refers to the percentage of sequence identity between two nucleic acid and/or polypeptide sequences. To determine the sequence identity of two nucleic acid sequences, the sequences are aligned for optimal comparison purposes (e.g., gaps can be introduced in the sequence of a first nucleic acid sequence for optimal alignment with a second nucleic acid sequence). The nucleic acid residues at corresponding nucleic acid positions are then compared. When a position in the first sequence is occupied by the same nucleotide as the corresponding position in the second sequence, then the molecules are identical at that position. The sequence identity between the two sequences is a function of the number of identical positions shared by the sequences (i.e., % identity=number of identical overlapping positions/total number of positions X 100%). In one embodiment, the two sequences are the same length. The determination of sequence identity between two sequences can also be accomplished using a mathematical algorithm.

The percent identity optionally exists over a region of the sequences that is at least about 50 residues in length, more preferably over a region of at least about 100 residues, and most preferably the percent identity exists over at least about 150 residues. In an especially preferred embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et at, *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990), These initial neighborhood word hits act as seeds for initiating searches to find longer HSPs containing them. The word hits are then extended in both directions along each sequence for as far as the cumulative alignment score can be increased. Cumulative scores are calculated, using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 1 1 an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

As used herein, the terms "a" or "an" in relation to an object mean a representative example from a collection of that object.

II. Methods

The present inventors have shown that complementing an *Arabidopsis* mutant lacking endogenous starch branching enzymes with each of two maize starch branching enzymes, ZmSBEI and ZmSBEIIB, and with a combination of both, results in a significant increase in *Arabidopsis* biomass accumulation and oilseed production.

Accordingly, one aspect of the present disclosure provides a method of increasing the biomass, seed production and/or oil production of a plant cell, plant or plant part comprising:

(a) transforming the plant cell, plant or plant part with a nucleic acid molecule encoding an exogenous starch-branching enzyme, and (b) expressing the transformed gene in the plant cell, plant or plant part.

In one embodiment, the plant cell, plant or plant part has reduced activity or expression of at least one endogenous starch-branching enzyme.

Transformation is a process for introducing exogenous (also known as heterologous) nucleic acid molecules into a plant cell, plant or plant part. Transformed bacterial plant cells, plants, and plant parts are understood to encompass not only the end product of a transformation process, but also transgenic progeny thereof. "Transformed," "transgenic," and "recombinant" refer to a host organism such as a plant cell, plant or plant part into which a heterologous nucleic acid molecule has been introduced. The nucleic acid molecule can be stably integrated into the genome of the host or the nucleic acid molecule can also be present as an extrachromosomal molecule.

Methods of transformation are well known in the art. In one aspect of the present disclosure, transformation comprises introducing into a plant cell, plant, or plant part an expression construct, or expression cassette, comprising an exogenous nucleic acid molecule to obtain a transformed, plant cell, plant, or plant part expressing the protein encoded by the nucleic acid molecule.

A. Expression Cassettes

Nucleic acid molecules intended for expression in transgenic plants are first assembled in expression cassettes with suitable regulatory sequence that allow for expression in plants. These expression cassettes can then be easily transferred to the plant transformation vectors described below. The following is a description of various components of typical expression cassettes.

Promoters: The selection of the promoter used in expression cassettes will determine the spatial and temporal expression pattern of the transgene in the transgenic plant. Selected promoters will express nucleic acid molecules in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. Examples of constitutive promoters (promoters that drive constitutive expression) that may be used in expression constructs are well known in the art and include, but are not limited to, the CaMV 35S Promoter, the Ubiquitin Promoter and the Actin Promoter. Inducible promoters (promoters that allow inducible expression) are well known in the art and include, but are not limited to, PR-1 Promoters, Ethanol-Inducible Promoter and Glucocorticoid-Inducible Promoters.

Transcriptional Terminators: A variety of transcriptional terminators are available for use in expression cassettes. These are responsible for the termination of transcription beyond the gene and correct mRNA polyadenylation. Appropriate transcriptional terminators are those that are known to function in plants and include the CaMV 35S terminator, the tml terminator, the nopaline synthase terminator and the pea rbcS E9 terminator. In addition, a gene's native transcription terminator may be used.

Sequences for the Enhancement or Regulation of Expression: Numerous sequences have been found to enhance gene expression from within the transcriptional unit and these sequences can be used in conjunction with the genes of this invention to increase their expression in transgenic plants.

Targeting of the Gene Product Within the Cell: Various mechanisms for targeting gene products are known to exist in plants and the sequences controlling the functioning of these mechanisms can be included in the expression cassettes.

B. Construction of Plant Transformation Vectors

Numerous transformation vectors available for plant transformation are known to those of ordinary skill in the art, and the nucleic acid molecules pertinent to this disclosure can be used in conjunction with any such vectors. The selection of vector will depend upon the preferred transformation technique and the target species for transformation. For example, a Ti plasmid is used for *Agrobacterium*-mediated transformation.

In one exemplary embodiment, the pB7WG2D.1 vector is used (for example, pB7WG2D-SBEIIb and/or pB7WG2D-SBEI), pB7WG2D.1 includes, in order, (1) a 35S promoter, (2) attR1 and attR2 sites disposed downstream of the 35S promoter, (3) a 35S terminator, (4) a "bar" marker gene (BASTA, phosphinothricin resistance), a selectable marker in plants, and (5) a marker gene, SmSpR (spectinomycin), a selectable marker in bacteria, particularly Agrobacterium.

C. Transformation

Once a polynucleotide of interest has been cloned into an expression system, it is transformed into a plant cell.

For example, the present examples describe *Agrobacterium*-mediated transformation. *Agrobacterium*-mediat transformation is well known in the art. The *Agrobacterium*-mediated transformation process can include, for example, inserting the gene of interest into a Ti-plasmid, introducing plasmid into *Agrobacterium* and then introducing the transformed *Agrobacterium* to plant cells to allow transfer of T-DNA into plant chromosomes.

Other methods of transformation include, but are not limited to, methods of direct DNA uptake wherein DNA is directly introduced into plant cells or tissues by particle bombardment, inducement by electric shock, use of micropipette systems, glass fibers or silicon carbide whisker transformation or by direct incubation of DNA with germinating pollen.

The present methods contemplate the transformation of nucleic acid molecules encoding starch branching enzymes (SBEs). In higher plants, turnover of starch is based on the cooperation of at least 30 enzymes. Among these, two types of starch branching enzymes can often be distinguished and are frequently designated as class I and class II (Zeeman et al. 2010; Tomlinson and Denyer 2003).

Examples of starch branching enzymes that can be transformed using the methods described herein include starch branching enzymes from cereal plants such as maize (*Zea mays*), wheat (*Triticum aestivum*), barley (*Hordeum vulgare*), rice (*Oryza sativa*), oat (*Avena sativa*), rye (*Secale cereal*) or sorghum (*Sorghum bicolor*). The starch branching enzymes are exogenous, or not native, to the plant cell, plant or plant part being transformed. For example, in one embodiment, starch branching enzymes from a cereal plant are transformed into an oilseed crop.

Other examples of starch branching enzymes that can be transformed using the methods described herein include starch branching enzymes from non-cereal plants, including, but not limited to, starch branching enzymes from bean (*Phaseolus vulgaris*), pea (*Pisum sativum*) and potato (*Solarum tuberosum*).

In one embodiment, a plant cell, plant or plant part is transformed with starch branching enzyme I from maize (*Zea mays*) (also referred to as ZmSBEI). ZmSBEI has accession number NP_001105370.1 and is encoded by the nucleotide (cDNA) sequence set out in SEQ ID NO: 1. The amino acid sequence of ZmSBEI is set out in SEQ ID NO: 2.

In another embodiment, a plant cell, plant or plant part is transformed with starch branching enzyme IIb from maize (*Zea mays*) (also referred to as ZmSBEIIb). ZmSBEIIb has GenBank accession number AAC33764.1 and is encoded by the nucleotide (cDNA) sequence set out in SEQ ID NO: 3. The amino acid sequence of ZmSBEIIb is set out in SEQ ID NO: 4.

In yet another embodiment, a plant cell, plant or plant part is transformed with both starch branching enzyme I and starch branching enzyme IIb.

In another embodiment, a plant cell, plant or plant part is transformed with a homologue to maize starch branching enzyme I and/or a homologue to maize starch branching enzyme IIb. As used herein, the term "homologue" refers to two or more nucleic acid sequences with identity to each other or to two or more amino acid sequences with identity to each other.

In another embodiment, a plant cell, plant or plant part is transformed with an ortholog to maize starch branching enzyme I and/or an ortholog to maize starch branching enzyme IIb. As used herein, the term "ortholog" relates to homologous genes or proteins in different organisms due to an ancestral relationship.

In another embodiment, a plant cell, plant or plant part is transformed with a nucleic acid molecule that has at least 70%, 80%, 85%, 90%, 95% or 99% sequence identity to SEQ ID NO: 1 (maize starch branching enzyme I). In another embodiment, a plant cell, plant or plant part is transformed with a polynucleotide that has at least 70%, 80%, 85%, 90%, 95% or 99% sequence identity to at least 100, 250, 500, 1000, 1500, 2000 or 2250 contiguous residues of SEQ ID NO: 1. In another embodiment, a plant cell, plant or plant part is transformed with a nucleic acid molecule that comprises, consists essentially or consists of SEQ ID NO: 1.

In another embodiment, a plant cell, plant or plant part is transformed with a nucleic acid molecule that has at least 70%, 80%, 85%, 90%, 95% or 99% sequence identity to SEQ ID NO: 3 (maize starch branching enzyme IIb). In another embodiment, a plant cell, plant or plant part is transformed with a polynucleotide that has at least 70%, 80%, 85%, 90%, 95% or 99% sequence identity to at least 100, 250, 500, 1000, 1500, 2000 or 2250 contiguous residues of SEQ ID NO: 3. In another embodiment, a plant cell, plant or plant part is transformed with a nucleic acid molecule that comprises, consists essentially or consists of SEQ ID NO: 3.

In another embodiment, a plant cell, plant or plant part is transformed with a first nucleic acid molecule that has at least 70%, 80%, 85%, 90%, 95% or 99% sequence identity to SEQ ID NO: 1 or at least 100, 250, 500, 1000, 1500, 2000 or 2250 contiguous residues of SEQ ID NO: 1 and a second nucleic acid molecule that has at least 70%, 80%, 85%, 90%, 95% or 99% sequence identity to SEQ ID NO: 3 or at least 100, 250, 500, 1000, 1500, 2000 or 2250 contiguous residues of SEQ ID NO: 3. In another embodiment, a plant cell, plant or plant part is transformed with a first nucleic acid molecule that comprises, consists essentially of or consists of SEQ ID NO: 1 and a second nucleic acid molecule that comprises, consists essentially of or consists of SEQ ID NO: 3.

In another embodiment, a plant cell, plant or plant part is transformed with a nucleic acid molecule encoding for at least one of the starch branching enzymes listed in the Table below:

TABLE 1

3Starch branching enzymes

| Source | Enzyme | Accession Number |
| --- | --- | --- |
| Zea mays | SBEI, starch branching enzyme I | NP_001105370.1 |
| Zea mays | SBEIIb, starch branching enzyme IIb | AAC33764.1 |
| Zea mays | SbeIIa, starch branching enzyme IIa | AAB67316.1 |
| Triticum aestivum | Sbe1, starch branching enzyme I | AF286317.1 |
| Triticum aestivum | SbeIIa, starch branching enzyme IIa | AF338432.1 |
| Triticum aestivum | SbeIIb, starch branching enzyme Iib | AY740401.1 |
| Hordeum vulgare | Sbe1, starch branching enzyme I | AY304541.1 |
| Hordeum vulgare | SbeIIa, starch branching enzyme IIa | FN179383.1 |
| Hordeum vulgare | SbeIIb, starch branching enzyme IIb | AF064561.1 |
| Oryza sativa | Sbe1, starch branching enzyme I | AF136268.1 |
| Oryza sativa | Sbe4, starch branching enzyme 4 | AB023498.1 |
| Oryza sativa | Sbe3, starch branching enzyme 3 | D16201.1 |
| Sorghum bicolor | SbeI, starch branching enzyme I | XM_2439014.1 |
| Sorghum bicolor | SbeIIa, starch branching enzyme IIa | XM_002447727.1 |
| Sorghum bicolor | SbeIIb, starch branching enzyme IIb | AY304540.1 |
| Solanum tuberosum | Sbe1, starch branching enzyme 1 | NM_001288254.1 |
| Solanum tuberosum | Sbe2, starch branching enzyme 2 | NM_001288538.1 |
| Pisum sativum | Sbe1, starch branching enzyme 1 | X80009.1 |
| Pisum sativum | Sbe2, starch branching enzyme 2 | X80010.1 |
| Phaseolus vulgaris | starch branching enzymes | AB029549.1 |
| Avena sativa | starch branching enzymes | |
| Secale cereale | starch branching enzymes | |

In one of the examples of the present disclosure, two starch branching enzymes endogenous to *Arabidopsis* (AtSBE2.1 and AtSBE2.2) are replaced with the maize starch branching enzymes described above. Accordingly, in another aspect of the disclosure, the plant to be transformed has reduced, or no, activity or expression of at least one endogenous starch-branching enzyme. In one embodiment, reduced, or no, activity or expression of at least one endogenous starch-branching enzyme results in a plant that is unable to synthesize leaf starch or has a reduced ability to synthesize leaf starch.

Methods of reducing or eliminating activity or expression of a gene are well known in the art. In a preferred example, a null mutant of at least one endogenous starch-branching enzyme is generated. Other methods include generating loss of function mutants and exposing the plant to agents (for example, chemical compounds or targeted RNA molecules) that reduce the expression of the gene or the expression or activity of the gene product.

In one embodiment, knockout mutants are created by applying the CRISPR (clustered regularly interspaced short palindromic repeat)/Cas (CRISPR-associated) system to at least one endogenous starch-branching enzyme. Methods of using the CRISPR system are well known to those skilled in the art and include, for example, the CRISPR/Cas9 toolkit generated by Xing et al.[64]

CRISPR can be applied by co-delivery of both the sgRNA and Cas9 which are subcloned into one binary vector. In one embodiment, two constructs are created, each of which targets a different endogenous starch-branching enzyme. In another embodiment, a single construct is created which targets both endogenous starch-branching enzymes.

A person of skill in the art will appreciate that the steps of the disclosed methods can be performed in various orders. For example, in one embodiment, a plant cell, plant or plant part is first transformed with at least one exogenous starch-branching enzyme, and then at least one endogenous starch-branching enzyme a plant cell, plant or plant part is knocked out, or its activity or expression is otherwise reduced. In another embodiment, at least one endogenous starch-branching enzyme of a plant cell, plant or plant part is knocked out, or its activity or expression is otherwise reduced, and then the a plant cell, plant or plant part is transformed with at least one exogenous starch-branching enzyme.

Various plants can be transformed with the genes described herein. In one embodiment, the plant is a dicotyledon. In another embodiment, the plant is of the family Brassicaceae. Examples of plants in the family Brassicaceae include *Arabidopsis*, canola, camelina, mustard and rapeseed. In another embodiment, the plant is an oilseed crop. Oilseed crops are crops grown primarily for the oil contained in the seeds. Oilseed crops include, but are not limited to, canola, flaxseed, camelina, cotton, mustard, rapeseed, soybean, sunflower seed and palm.

The methods described herein produce a transformed plant cell, plant or plant part which has increased biomass, seed production and/or oil production compared to a wild-type plant cell, plant or plant part. The native or wild type plant is a plant not transformed with the exogenous nucleic acid molecules described herein. Optionally, the native or wild type plant has normal expression of endogenous starch branching enzymes.

III. Transgenic Plants

Another aspect of the present disclosure relates to transgenic plants, plant cells and plant parts obtained by the methods described herein and the seeds and progeny thereof. Plant parts include, but are not limited to, seeds, siliques, fruit, leaves, flowers, shoots, stems, roots, isolated plant cells, tissues and organs. Plant cells include cells which are derived and/or isolated from plant cell tissue or plant cell culture.

The disclosure provides a transformed plant cell, plant or plant part expressing at least one nucleic acid molecule encoding an exogenous starch-branching enzyme, wherein said transformed plant cell, plant or plant part has increased biomass, seed production and/or oil production compared to a wild-type plant cell, plant or plant part.

In one embodiment, the plant cell, plant or plant part has reduced activity or expression of at least one endogenous starch-branching enzyme.

The transformed plants and plant parts described herein have increased biomass, seed production and/or oil production compared to wild-type or native plants which have not been subjected to the methods described above.

In one embodiment, the transformed plant or parts thereof have increased size, height and/or mass as compared to a native or wild-type plant. In one embodiment, the size, height and/or mass of the transformed plant or parts is increased by at least 2%, 5%, 10%, 25%, 50%, 100%, 200%, 300%, 400% or 500% compared to a native or wild type plant or as compared to a predetermined standard. Mass is optionally measured by fresh weight and/or dry weight.

In another embodiment, the transformed plant or parts thereof have increased seed production as compared to a native or wild-type plant. In one embodiment, the number of seeds per plant, the number of siliques per plant and/or the number of seeds per silique of the transformed plant or parts is increased by at least 2%, 5%, 10%, 25%, 50%, 100%, 200%, 300%, 400% or 500% compared to a native or wild type plant. In another embodiment, the seed size and/or seed length of the transformed plant is increased by at least 2%, 5%, 10%, 25%, 50%, 100%, 200%, 300%, 400% or 500% compared to a native or wild type plant or as compared to a predetermined standard.

In another embodiment, the transformed plant or parts thereof have increased flowering as compared to a native or wild-type plant. In one embodiment, the number of flowers per transformed plant and/or the mean size of the flowers of the transformed plant is increased by at least 2%, 5%, 10%, 25%, 50%, 100%, 200%, 300%, 400% or 500% compared to a native or wild type plant or as compared to a predetermined standard.

In another embodiment, the transformed plant or parts thereof have increased oil production as compared to a native or wild-type plant. Increased oil production can reflect an increased number of oilseeds produced per plant as a consequence of increased flowering and/or silique formation. In one embodiment, the oil content of a plant is increased by at least 2%, 5%, 10%, 25%, 50%, 100%, 200%, 300%, 400% or 500% as compared to a native or wild-type plant or as compared to a predetermined standard.

In another embodiment, the transformed plant or parts thereof have increased oilseed production as compared to a native or wild-type plant. In one embodiment, the number of oilseeds per plant and/or the total seed weight per plant is increased by at least 2%, 5%, 10%, 25%, 50%, 100%, 200%, 300%, 400% or 500% as compared to a native or wild-type plant or as compared to a predetermined standard.

In yet another embodiment, the transformed plant or parts thereof have increased lipid accumulation and/or triacyl glycerol (TAG) yield as compared to a native or wild-type plant. In one embodiment, the lipid accumulation and/or triacyl glycerol (TAG) yield is increased by at least 2%, 5%, 10%, 25%, 50%, 100%, 200%, 300%, 400% or 500% as compared to a native or wild-type plant or as compared to a predetermined standard.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

A. Expression of Maize Starch Branching Enzymes in *A. Thaliana* Chloroplasts

Figure 1:
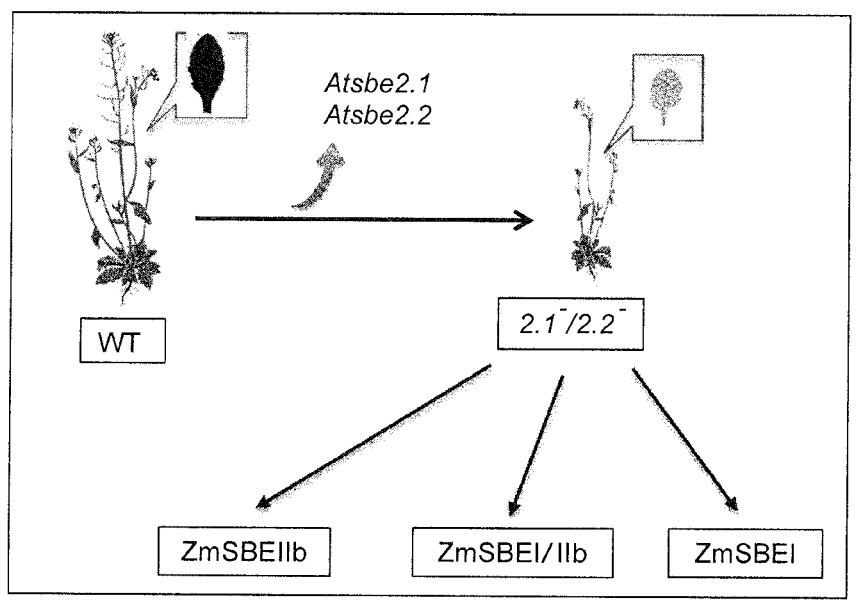
FIG. 1 outlines the generation of *Arabidopsis* transformants expressing maize branching isozymes. Wild type (WT) *Arabidopsis thaliana* (Col-0) plants possess the two branching isozymes (SBEs), designated as AtSBE2.1 and AtSBE2.2, and are capable of synthesizing transitory starch as indicated by a decolorized iodine stained leaf (upper row; left insert). Two single knock-out lines (both derived from Col-0) that are deficient in either AtSBE protein were crossed and a homozygous null mutant was generated lacking both AtSBE2.1 and AtSBE2.2. This null mutant which is unable to synthesize starch (upper row; right insert) was transformed with either ZmSBEI, ZmSBEIIb or with a combination of both maize-derived SBEs to obtain stable transformants (lower row).

The *Arabidopsis* sbe2.1/sbe2.2 double null mutant was generated using the Col-0 accession and subsequently used for all transformations. The mutant is unable to synthesize leaf starch (FIG. 1) and its phenotypic features are similar to those obtained in the Wassilewskija (Ws) background by Dumez et al. (2006). Using the Col-0 null mutant, stable transformant lines were produced by the floral dip method (Nature Protocols) that express maize endosperm-specific SBEs rather than the two endogenous BEs. Two plasmids were used, one encoding ZmSBEI, one ZmSBEIIb, transformed individually, or together. In all maize-derived constructs, the native transit peptide of the respective maize BE is encoded. All constructs are under the control of the cauliflower mosaic virus (CaMV) 35S promoter ensuring constitutive in planta expression.

Figure 2:
FIG. 2 shows phenotypic features of the wild type (WT), the null mutant (2.1-/2.2-), and the three maize SBEs expressing *Arabidopsis* plants (ZmSBEI, ZmSBEI/IIb, and ZMSBEIIb). (a) Representative shoots of mature plants (7 weeks old). (b) Representative rosettes of non-flowering plants (2 to 3 weeks old). (c) Representative leaves of plants (2 to 3 weeks old) stained with iodine following decolourization to visualize starch. Leaves were harvested at the end of the 16 h light period (left) and at the end of 8 h dark (right). (d) Western blots of leaf extracts of 2 to 3 weeks old plants probed with an anti-peptide antibody that is specific to the *Arabidopsis* SBEs or with anti-maize SBE antibodies.
Figure 6:
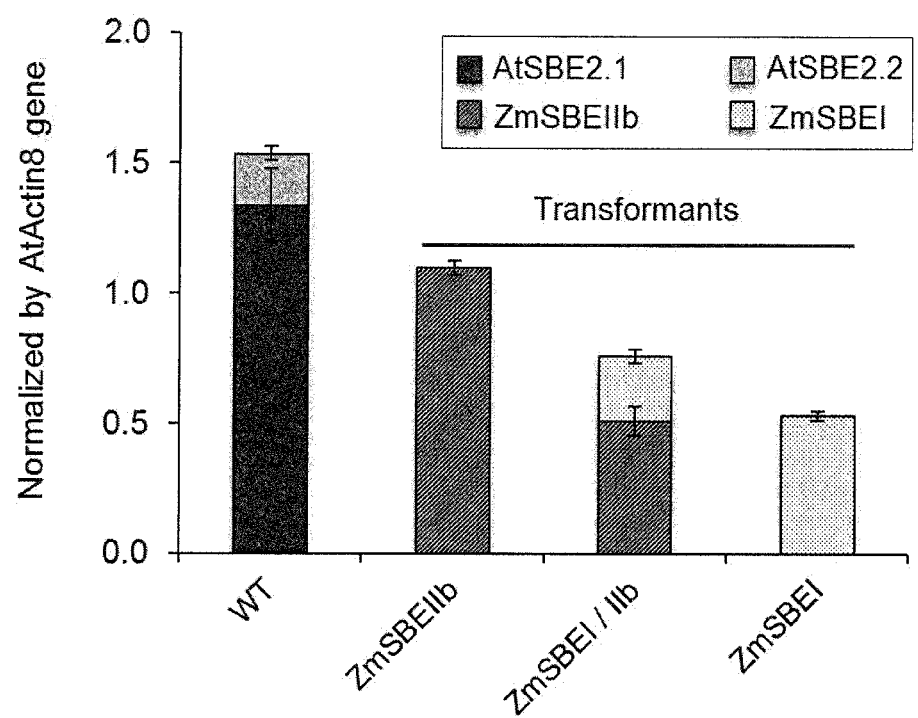
FIG. 6 shows relative transcript levels of the various transgene products. Leaves from 3-4 week old plants were harvested in the middle of light periods (16/8 hours light/dark strategy). Transcript levels are based on that of the transcript of the AtActin8 gene. Average values±SD.

Transformants were selected on suitable antibiotics and verified using real-time PCR assays of transcript abundance. All data described below have been obtained with the homozygous T4 generation and similar results were obtained from two further generations demonstrating the stability of the transformation. In the leaves of these *Arabidopsis* plants, transcript levels of each of the ZmSBE genes are similar to AtSBE2.1 and AtSBE2.2 (FIG. 6). Measurement of the total SBE catalytic activity and western blot analysis of transformants using isoform or isopeptide-specific anti-ZmSBE antibodies show that products of all three constructs are processed to the mature size and form functionally active enzymes (FIG. 2d). The presence of transitory starch in the leaves of all three transformed lines (FIG. 2c) demonstrates that, in the sbe2.1/sbe2.2 null mutant, starch biosynthesis is restored by expressing a single cDNA or a combination of both cDNAs derived from *Zea mays*.

B. *A. Thaliana* Plants Expressing Endosperm-Specific, Maize Starch Branching Enzymes Show Enhanced Biomass and TAG Production The most obvious macroscopic phenotype of the ZmSBE transformants is the enhanced biomass production. In mature plants, enhanced biomass is due to an increase in height and more shoots per plant (FIG. 2a). At an earlier state, leaves of all transformants are larger than the wild-type counterpart resulting in a substantial increase in rosette diameter (FIG. 2b).

Growth-related effects are stable over several generations for all of the transgenic lines. Shoot fresh and dry weights of transgenic plants are significantly higher than wild-type or null mutant plants (FIG. 3a). Transformation with either ZmSBEIIb or a combination of ZmSBEIIb and ZmSBEI results in similar fresh and dry weights both of which are significantly higher than the wild type control. However, the A. thaliana mutant transformed with ZmSBEI only, exhibits the greatest (almost 3-fold) increase in biomass.

The null mutant possesses a significantly reduced total oil yield per plant compared with wild-type plants. Strikingly, complementation with either ZmSBEIIb or with the combination of ZmSBEIIb and ZmSBEI, leads to significant increases in total oil yield, and transformation with ZmSBEI increases total oil production per plant more than two-fold as compared to the wild type (FIG. 4a).

Oil production in all transformants is reflected in total seed yield (FIG. 3c) which in turn arises from a marked increase in the number of siliques per plant (wild type: 271±54; null mutant: 273±51; ZmSBEIIb: 815±112; ZmSBEIIb/ZmSBEI: 705±109; ZmSBEI: 1,260±211; n=15; FIG. 3c), the number of seeds per plant (wild type 11,440±103; ZmSBEIIb: 27,740±241; in ZmSBEI: 50,134±274 (n=15 for all), and increases in the weight of seeds per plant (wild type: 0.26 gram; null mutant: 0.11 gram; ZmSBEIIb: 0.46 gram; ZmSBEIIb/ZmSBEI: 0.49 gram; ZmSBEI: 0.78 gram; n=15; FIG. 3b). Silique length is modestly reduced in two of the transformed lines but more strongly in the null mutant (FIG. 3d). The number of seeds per silique is similar for WT, ZmSBEI and the double transformant but is strongly decreased in the null mutant (FIG. 3e). Differences in seed size are minor (FIG. 3f) but the average seed weight (measured as the weight of 1,000 seeds each) is reduced by at most 31% of the wild type control. The ZmSBEI transformant has the lowest average seed weight (FIG. 3g).

Despite the lower average weight, oil production per plant is massively increased with the ZmSBEI transformant being most productive (FIG. 4a). Whilst the total oil content per plant increases in all transformants the pattern of fatty acids remains unchanged (FIG. 4b).

Figure 5:
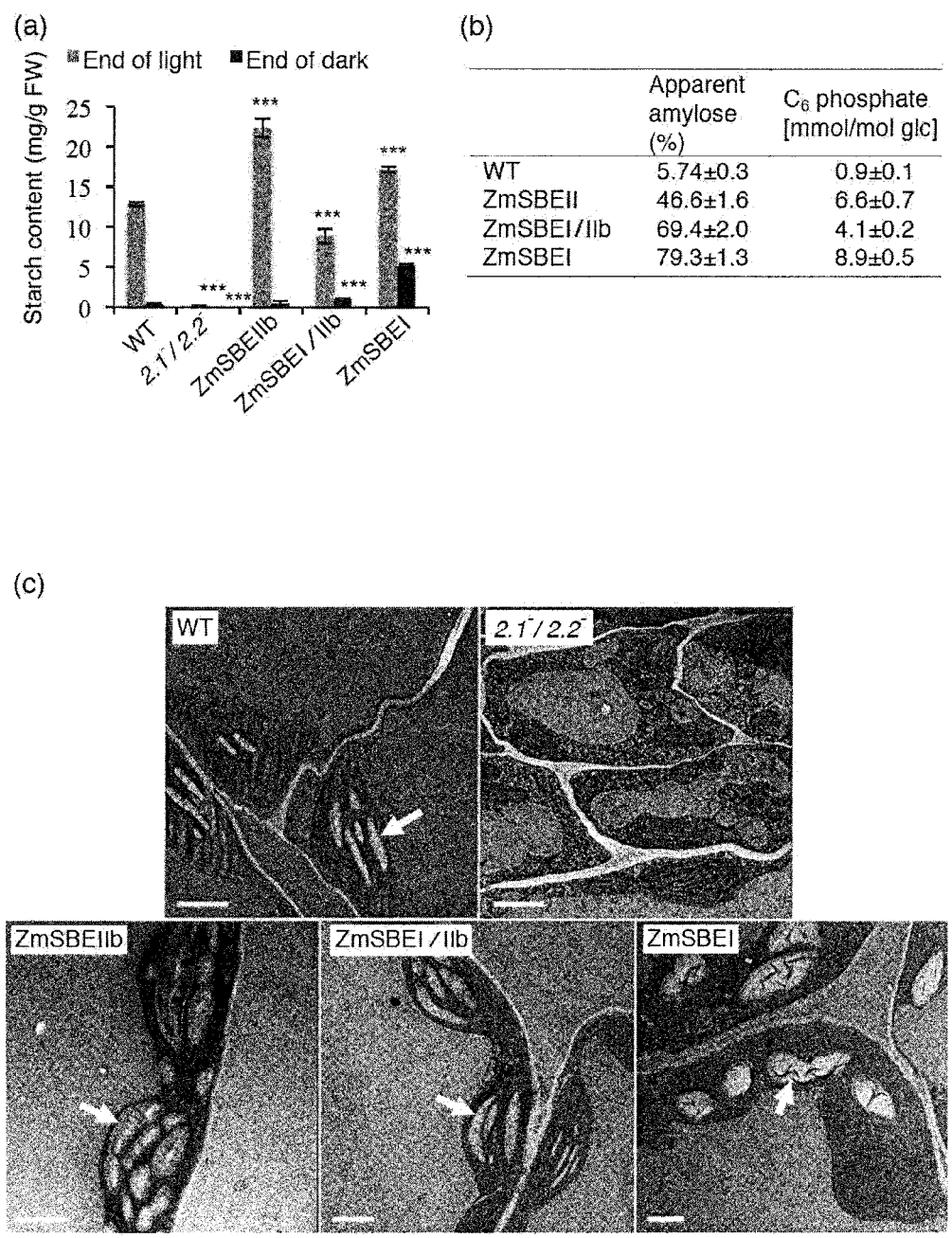
FIG. 5 shows starch content, in situ starch granules, and starch properties of rosette leaves of the various *Arabidopsis* lines. (a) Leaf starch content at the end of the 16 h light period (grey) and at the end of the 8 h dark period (black). (b) Apparent amylose content of leaf starch isolated at the end of the 16 h light period. In (a) and (b), three independently generated lines have been analyzed, and three pooled replicates of starches for each transformant. Mean values±SD. (c) TEM micrographs of leaf sections. Leaf materials were sampled in the middle of the light period and fixed immediately. Starch granules are marked with a white arrow. Scale bar, 2 µm. (d) Size distribution of starch granules extracted from leaves at the end of the light period.

C. Expression of Maize Starch Branching Enzymes in *A. thaliana* Results in an Altered Leaf Starch Metabolism A single endosperm-specific SBE isoform from maize is sufficient to restore the capacity for starch synthesis in *Arabidopsis* leaves. Plants transformed with either ZmSBEIIb or ZmSBEI accumulate significantly more leaf starch during the day as compared with wild-type plants, whereas in double transformants (expressing both ZmSBE isoforms) the leaf starch content at the end of the day is slightly reduced compared to the single mutants (FIG. 5a). All transformants (and wild type) metabolize leaf starch during the 8 h dark period, although residual starch levels differ. At the end of the dark period, the wild-type and the ZmSBEII transformant retain approximately 2.5% of the starch per leaf fresh weight, whereas in the ZmSBEI/II and ZmSBEI transformants starch degradation is not so complete (12% and 30% remaining, respectively; FIG. 5a).

In each of the transformants, however, the assimilatory starch formed deviates from that of the wild type control in terms of quantity and quality indicating an altered starch metabolism.

Figure 7:
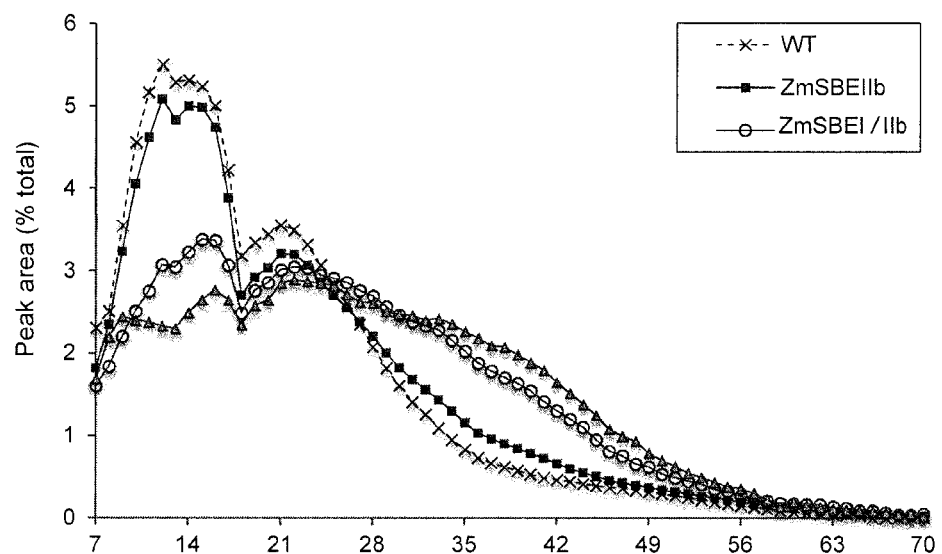
FIG. 7 shows side chain pattern of leaf starch from the various *Arabidopsis* lines. (a) Molar percentage of each side chain plotted against degree of polymerization. (b) Relative molar difference of the side chains using the respective chains from the wild type starch as reference.
Figure 7:
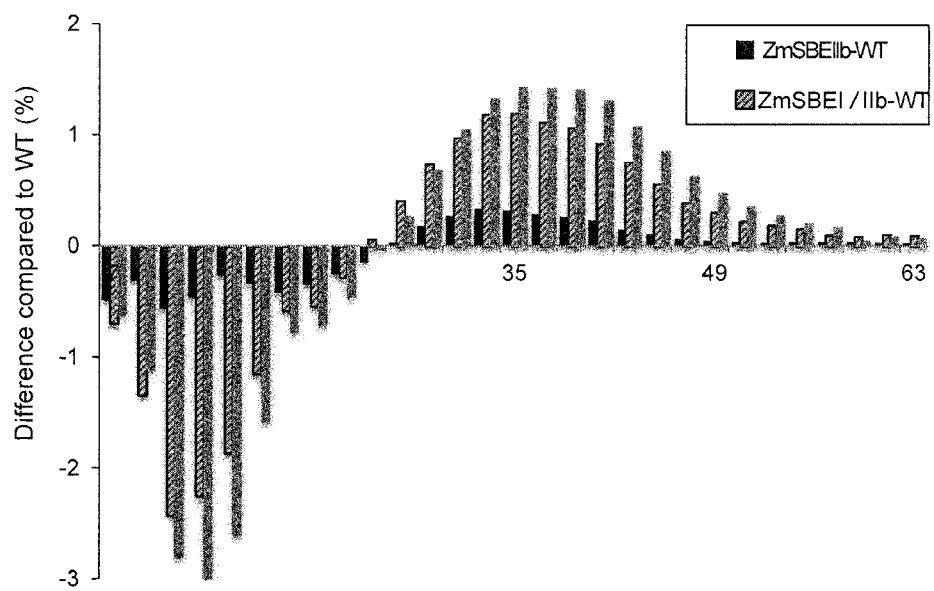

A common, and striking, characteristic of the leaf starches produced by the transformed plants is a relative increase in apparent amylose content of the starch by between 8- and 13-fold, with transformants expressing SBEI (singly or in combination with SBEIIb) showing the highest levels of apparent amylose (FIG. 5b). Following starch solubilization and enzymatic debranching, the side chain pattern was determined by anion-exchange chromatography. As compared to the wild type control, starch from all transformants is deprived of small chain lengths but chains having a size of more than 25 glucosyl moieties are enriched. This effect is most pronounced in transformants expressing ZmSBEI only or ZmSBEI/ZmSBEIIb (FIG. 7). Transformation of *A. thaliana* with ZmSBEs results in increases in starch-based glucosyl 6-phosphate esters, plants transformed with ZmSBEI alone showing a 10-fold increase in C6 phosphate (FIG. 5b).

All *Arabidopsis* plants transformed with one or both ZmSBE(s) deposit starch in the chloroplast stroma (as does the wild type) but exhibit altered granule morphology and changed physicochemical characteristics of starch (FIG. 5b and c). Most notably, the ZmSBEI transformant displays a largely altered granule morphology as the large granules appear to be more rounded and cracked or fissured as compared to the wild-type and SBEI/II lines (FIG. 5c). The latter starch granules are ellipsoid and more similar to the wild type control (Zeeman et al. 2010).

Laser scattering was used to measure the apparent granule size. Using this method, an increase in the frequency of larger granules in all transformants was observed (FIG. 5d). Intriguingly, the double transformant, ZmSBEI/II, appears to possess two populations of starch granules (FIG. 5d), one of which aligns closely with the population of granules observed in ZmSBEIIb transformants and the other, smaller sized population with the wild type control and ZmSBEI transformant.

D. Discussion

Almost all higher plants possess three major sinks for photosynthetically fixed carbon: cellulose/hemicellulose (cell walls), starch and TAG. The relative strength of the sinks, however, varies depending on developmental stage and plant species[25]. All these biopolymers produced by crop plants are increasingly relevant for various (bio)technological uses.

Here unexpected findings are reported in an oil-seed, *A. thaliana*, obtained by the replacement of endogenous starch synthesizing SBEs with endosperm-specific SBEs from maize. Expression of maize SBEs in *Arabidopsis* restores transitory leaf starch biosynthesis but also results in significant changes in growth and development, increased biomass and, most significantly, total seed oil production per plant. Brassicaceae synthesize transient starch in leaves as well as a small amount in developing embryos[35]. *Arabidopsis* AtSBE2.1 and AtSBE2.2 were replaced by ZmSBEI and ZmSBEIIb which in the maize endosperm fulfill distinct functions in storage starch accumulation and differ in some kinetic properties, such as the preferred length of the glucan chain transferred and presumably impart selective advantages[36]. As an example, the presence of SBEI in developing maize endosperm, promotes subsequent seedling vigor[37]. Likewise, SBEIIb is restricted to storage starch forming tissues, and SBEIIa in leaves[38]. SBEIIa is also found in seeds of cereals. It is primarily a leaf enzyme but is also a major protein, for example, in wheat and barley endosperm. When introduced into the null mutant of *Arabidopsis*, each of the two maize-derived SBE isozymes is capable of restoring assimilatory starch biosynthesis. These results extend previous observations that in *Arabidopsis* (Ws background) each of the two endogenous SBE isoforms (AtBE2.1 and AtBE2.2) can be deleted without disturbing transitory starch biosynthesis and strongly suggest functional redundancy[34].

Although all transformants generated in this study (Col-0 background) are capable of forming transitory starch, the amount and type of starch is altered compared to the wild type. Based on the increase in plant size as well as the amount of starch at the end of the light period, all transformants accumulated more leaf starch, with a much higher proportion of apparent amylose, rising from 6% to nearly 80% in the case of ZmSBEI plants. Without being bound by theory, it is, however, highly likely that the increased 'apparent amylose' content reflects amylopectin molecules with an altered structure rather than amylose itself. This conclusion is based on the side chain pattern in which the relative proportion of short chains is decreased but longer chains (DP>25) are enriched (FIG. 7). Supportive evidence for this view is derived from examination of the content of glucan-based glucosyl 6-phosphate residues, which are elevated 5-10 fold in the transformants (FIG. 5b). Unlike amylose, amylopectin is known to be phosphorylated and an altered ratio of glucan elongating and branching reactions is associated with an increased total phosphate content of starch[39].

In the leaves of the all Arabidopsis transformants generated in this study larger starch granules occur (FIG. 5c). Intriguingly in the double-transformants, a bimodal frequency distribution is observed. This would be consistent with the independent actions of the individual enzymes and, without being bound by theory, might imply that, in some way, their metabolic functions are kept separate in the chloroplasts of the double transformants though the underlying mechanism is unclear. The starch granules formed, however, remain substantially smaller than the single granules produced per amyloplast in maize endosperm[40], suggesting that in chloroplasts other factors are involved in granule size and number determination.

Figure 3:
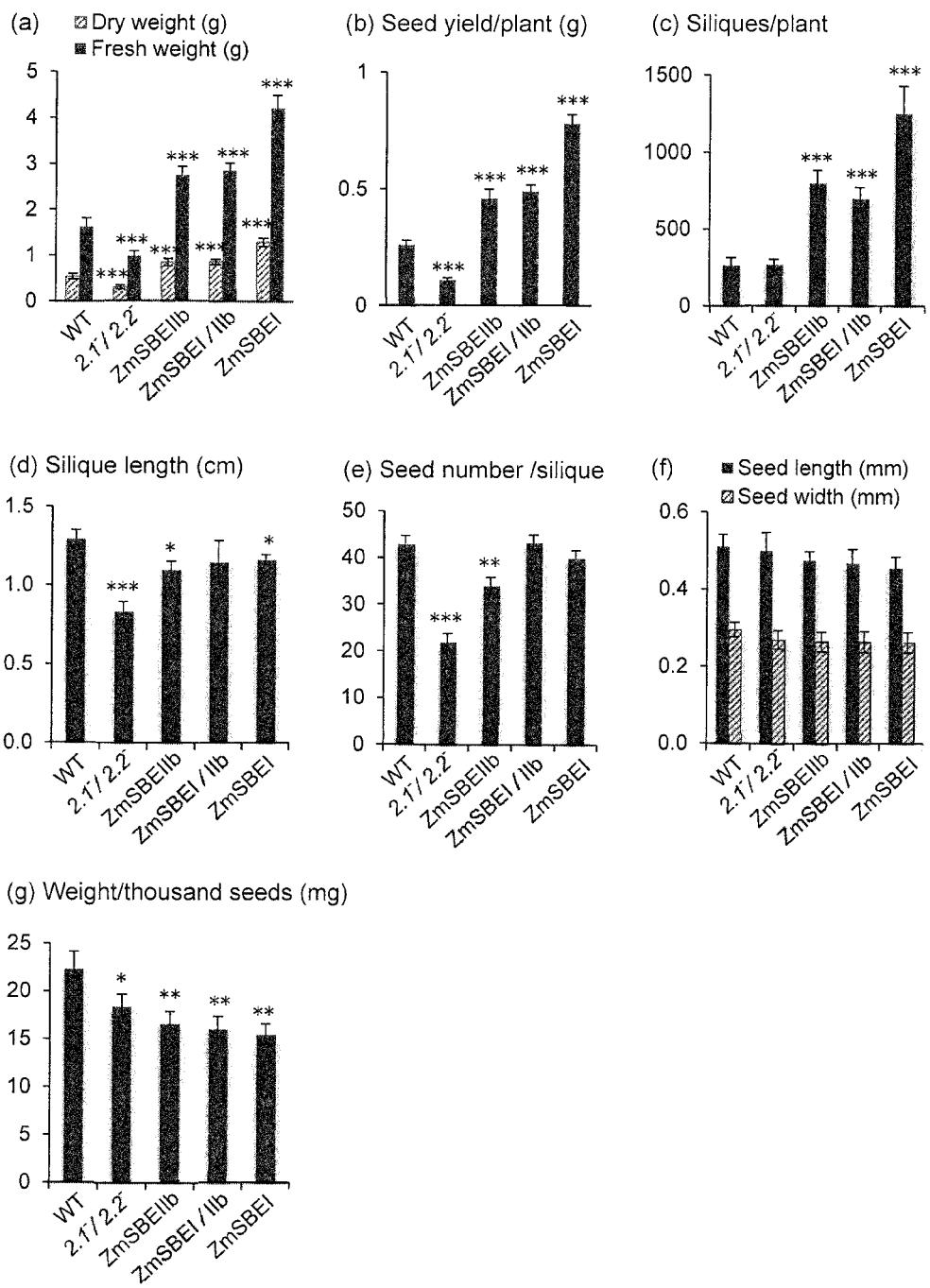
FIG. 3 shows phenotypic features of shoots, siliques, and seeds from the transformants, the null mutant, and the wild type control. For each type of transformant, data are derived from three independently generated transgenic lines. (a) Fresh and dry weight of the shoots given in g per plant. (b) Seed yield per plant given in grams (c) Number of siliques per plant. (d) Length of the siliques given in cm. (e) Number of seeds per silique. (f) Length and width of seeds given in mm. (g) Weight of thousand seeds given in g. Average values of at least five plants are given±SD. Statistical significance related to the values of the wild type control are indicated as *, $P<0.05$; , $P<0.01$: *, $P<0.001$ according to Student's t-test. Plants were grown in soil for 6 weeks.
Figure 4:
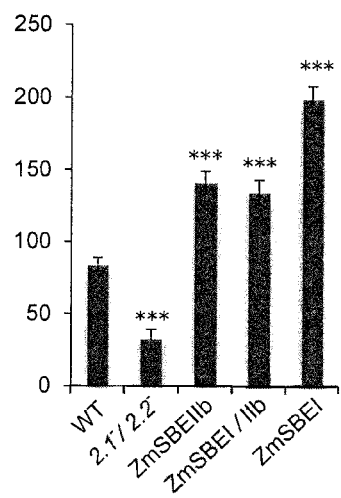
FIG. 4 shows oil production and fatty acid composition of seeds from the various *Arabidopsis* lines. (a) Oil production per plant was calculated from seed yield per plant and TAG contents on the weight value measured by NMR. (b) Fatty acid composition. Results are the average values of at least three pooled biological replicates±SD.
Figure 4:
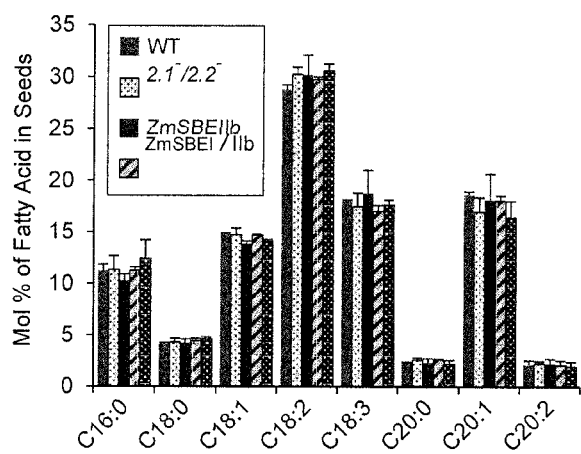

The alteration in starch metabolism, as described above, is associated with an enhanced biomass production and, even more dramatically, with an increase in lipid accumulation per plant (FIG. 4). The seed number per silique, and TAG yield per seed are largely unaltered or even reduced compared with wild-type plants (FIG. 3). Without being bound by theory, given the unequivocal increase in silique and total seed numbers per plant, it may be that the reduction in weight of individual seeds is a result of some other nutrient limitation. Thus it appears that the elevated TAG yield of the transformants is a consequence of a general enhancement in plant biomass and in flowering. Many studies have demonstrated the crucial role of plant carbohydrate metabolism in influencing floral induction and subsequent inflorescence development[69, 70]. If the nutritional demands of reproduction exceed the photosynthetic resources allocated to the ovule, then seeds will abort[41, 42]. Previous studies on cereals and oilseed crops have shown that the supply of photosynthate is crucial in seed development and filling[29, 43-46]. Thus, expression of maize SBEs appears to alter carbon partitioning in Arabidopsis such that more carbon is available for growth, in particular at key developmental stages such as flowering.

In conclusion, the data show that transgenic replacement of endogenous SBEs of the dicotyledonous oilseed A. thaliana, with cereal endosperm-specific SBE isoforms from maize, leads to dramatic increases in biomass and a doubling of TAG yield.

A. thaliana is a well-established model organism in plant biology. As is well understood in the art, discoveries made in A. thaliana are readily transferable to many other plant species. Accordingly, the methods disclosed within that are exemplified in A. thaliana, are also useful in other plants including but not limited to, plants of the mustard family Brassicaceae and oilseed plants. For example, there is a close genetic relationship between A. thaliana and domesticated species such as canola.

The work presented here shows that replacing endogenous SBEs of plants of the family Brassicaceae with SBEs from cereal plants enhances biomass, oil production and TAG yield. In addition, given that A. thaliana is an oilseed plant, the work presented here also shows that replacing endogenous SBEs of oilseed plants such as canola, camelina, cotton, flaxseed, mustard, rapeseed, soybean, sunflower seed or palm with SBEs from cereal plants enhances biomass, oil production and TAG yield.

E. Methods

Plant Material and Growth Condition

All experiments have been performed with Arabidopsis thaliana Accession Col-0 plants grown in growth chambers at 16 h light/8 h dark (23° C./18° C.) and a photon flux density of 140-150 μE m-2s-1, watering twice a week maintaining 50-60% humidity48. The null double mutant background used for transformation was generated by crossing single mutants lacking either AtSBE2.1 or AtSBE2.2. Homozygotes lacking both AtSBE2.1 and AtSBE2.2 were selected by PCR based targeting T-DNA insertions34. The full-length cDNAs coding for SBEI and SBEIIb proteins from developing maize endosperm were amplified and cloned into a binary vector pB7WG2D under a cauliflower mosaic virus (CaM) 35S promoter. Transgenic Arabidopsis were generated through Agrobacterium-mediated transformation constitutively expression the maize starch branching enzymes49. Transformants were selected on half-strength Murashige and Skoog medium containing 50 μg/ml of BASTA (glufosinate ammonium), and screened for segregation by staining leaf starch and PCR. Three independent homozygous lines of T4-generation homozygous plants from each transformant were used for further phenotype analysis.

Biomass Analysis

Heights of Arabidopsis plants were measured at 49 days after germination (DAG). Ten plants from each line and thirty in total were used for each transformant. Photographs for whole plants were taken from a representative size for each transformant. Rosette pictures were taken at 20 DAG for representatives of each transformant. Leaf starches were stained at 20DAG at the beginning and end of the light period[50].

Shoot fresh and dry weights were analyzed for five plants from each line and fifteen in total for each transformant. Shoot fresh weights were measured at 45 DAG and dry weights analyzed at maturity. Shoots were oven-dried at 70° C. to constant weight[51].

Seeds yield per plant, number of siliques, silique length and seeds number per silique were measured for five plants from each line and fifteen in total for each transformant. For silique length and seeds number per silique, 3 siliques were measured for each plant and 45 in total for each transformant.

Seed length and 1000 seeds weight were analyzed for mature seeds. Three pooled replicas (each pooled from 5 plants of in one line) were measured for each transformant by using a Master Sizer and Image-J software[52].

Oil Content Determination

Mature seeds of five plants from each line and fifteen in total for each transformant were analyzed for total amount of fatty acids. Aliquots of 100 mg seed samples were analysized using a Minispec nuclear magnetic resonance (NMR) analyzer (Minispec Mq10, Bruker Inc) calibrated for Arabidopsis seeds, and the composition of fatty acids in seeds analyzed using a gas chromatography flame ionization detector (GC-FID)[53].

Starch Analysis

Leaf starches were purified from rosettes of transgenic and wild type plants (28DAG). The amount of starch at the end of light and dark periods was quantified as glucose following solubilization and hydrolysis[54]. One pooled biological replicate per line, three for each transformant.

Apparent amylose content was determined from native starch solubilized in 90% (v/v) DMSO, followed by gel filtration chromatography on a Sepharose CL-2B gel permeation column (1.6×32 cm; Pharmacia, Uppsala, Sweden)[55]. Glucosyl 6-phosphate esters were determined in the starch hydrolysates by an enzymatic cycling assay[56].

Starch granule sizes were measured by means of laser scattering using the Master Sizer (Malvern Mastersizer 2000, Malvern Instruments Ltd., U K)[57].

Protein Analysis

SDS-PAGE and immunoblotting were performed as previously described[58].

Real-Time Reverse Transcription-PCR (qRT-PCR)

Transcript levels of maize starch branching enzymes in the transgenic *Arabidopsis* were quantified by qRT-PCR. For each transformant, RNA was extracted from 2 replicated pools of 15 leaves (5 biological replicate leaves in each of 3 lines) using TRI-Reagent (Sigma-Aldrich, Mo., USA), followed by treated with RQ1 RNase-free DNase (Promega, Wis., USA) to remove any residual genomic DNA. The first strand cDNA was synthesized using qScript cDNA SuperMix (Quanta Biosciences) following the manufacturer's instructions[59]. A StepOnePlus Real-Time PCR system was used, and resulting data were normalized by actin8 gene[80]. Data were analyzed by the $2^{-\Delta C_T}$ method[61] to obtain fold difference in expression of starch branching enzymes in the transformants, double mutants and the wild type.

Primers for qRT-PCR were design by Primer Express 3.0 software (Applied Biosystem) and conservative sequences of the branching enzymes were omitted:

| Primer | Sequence | SEQ ID NO |
|---|---|---|
| AtSBE2.1_Forward | TCGGGATACTGTCTCTGACG | SEQ ID NO: 5 |
| AtSBE2.1_Reverse: | TCTCTGTTTCCTGGGCTTCT | SEQ ID NO: 6 |
| AtSBE2.2_Forward: | TCTCGACCTCTCAACACTGG | SEQ ID NO: 7 |
| AtSBE2.2_Reverse: | AAACTCCGCAGATTGTTTCC | SEQ ID NO: 8 |
| ZmSBEIIb_Reverse: | GGGACCACTCGAACTCTGTT | SEQ ID NO: 9 |
| ZmSBEIIb_Forward: | CTCAATTCCAGTCGGATGAA | SEQ ID NO: 10 |
| ZmBEI_Forward: | AAGAAGACAAGGAGGCAACG | SEQ ID NO: 11 |
| ZmBEI_Reverse: | GGTATCTTGATCGGATGGCT | SEQ ID NO: 12 |
| AtActin8_Forward: | GCCGATGCTGATGACATTCA | SEQ ID NO: 13 |
| AtActin8_Reverse: | CTCCAGCGAATCCAGCCTTA | SEQ ID NO: 14 |

Transmission Electron Microscopy (TEM)

Leaf materials were harvested in the middle of the light period at 28 DAG. Samples were immediately immersed in fixing solution overnight[62], followed by frozen in a high pressure freezer[63]. Mesophyll cell chloroplasts were viewed on an FEI Tecnai G2 F20 TEM, with a Gatan 4K CCD camera, and Gatan Digital Micrograph software used to record images.

Example 2

Expression of Maize SBE1 in *Brassica Napus*

Figure 8:
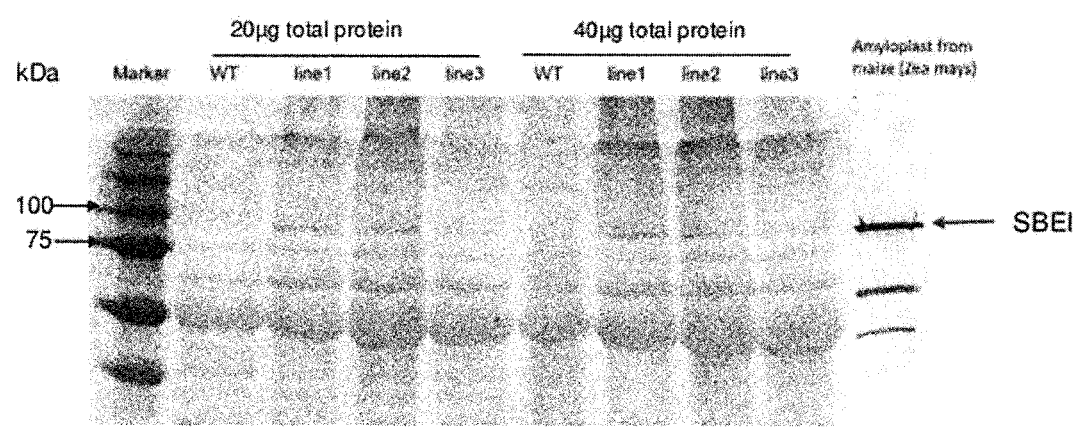
FIG. 8 shows total proteins extracted from *Brassica napus* leaves of wild type (WT) and three transgenic independent lines (line1, line2 and line3), which were separated on a 10% SDS-PAGE gel. The SBEI protein was characterized by immunoblot analysis using maize SBEI-specific antibodies.

Starting with a wild type *Brassica napus* background, stable transformant lines were generated by the floral spray method with GV3101 *agrobacterium* medium. Three positive transgenic lines were identified. Western blot analysis of transformants using isoform or isopeptide-specific anti-ZmSBE1 antibodies show that products of all three constructs are processed to the mature size and form functionally active enzymes, while the wild type control does not have this product (FIG. 8).

Example 3

Knockout of Endogenous SBEs from Canola

The CRISPR (clustered regularly interspaced short palindromic repeat)/Cas (CRISPR-associated) system has been applied to plants by co-delivering both the sgRNA and Cas9 which were subcloned into one binary vector. In this study, the CRISPR/Cas9 toolkit that was generated by Xing et al.[64] is used. To knockout the endogenous *Brassica napus* SBE2.1 and SBE2.2 that are located in both chromosome A and C, two strategies are applied (FIG. 9). One is to use two constructs CRISPR-A and CRISPR-B that target BnSBE2.1 and BnSBE2.2, respectively. The other strategy, CRISPR-C, is to apply one construct (CRISPR-C) to target both BnSBE2.1 and BnSBE2.2 simultaneously.

gRNA Expression Cassettes

Both CRISPR-A and CRISPR-B harbor four pieces of 20 bp target sequences with two from chromosome A and two from chromosome C, which constitute four gRNA expression cassettes in a tandem connection by using the method of Gibson assembly. CRISPR-C contains two pieces of 20 bp sequences targeting BnSBE2.1 and two sequences targeting BnSBE2.2, and they are homogeneous between chromosome A and C. The four gRNAs are driven by an order of promoters from *Arabidopsis* U6-26p, U6-29p, U6-1p, U6-26p and terminated by a same order of terminators U6-26t, U6-29t, U6-1t, U6-26t (FIG. 9). These cassettes can be easily assembled into the BsaI-linearized binary vectors in only one cloning step.

Construction of Plant Transformation Vectors

The vectors used in this example are designed for CRISPR/Cas9 expression. In the CRISPR-A embodiment, the pKSE401 vector is used (that is, four gRNA expression cassettes plus pKSE401). The four pieces of target sequence for BnSBE2. 1 are A05-1: G C ATCAAAG AAC AC ACTG G A (SEQ ID NO: 15), A05-2: GGGAATTA-CAACGAGTACTT (SEQ ID NO: 16), C04-1: GATCGTCGTTGAAACTTGGG (SEQ ID NO: 17) and C04-2: GTATTTCCACTCTGGATCGC (SEQ ID NO: 18). pKSE401 is a CRISPRICas9 binary vector derived from pCAMBIA. It includes, in order, (1) gRNA scaffold for insertion of target sequence (AtU6-26 promoter), (2) 2X35S promoter, (3) Zea mays codon-optimized Cas9, (4) a pea rbcS E9 terminator, (5) a Kanarnycin-resistence gene as a selectable marker in plants, and (6) a marker gene, KanR (Kanamycin), a selectable marker in bacteria.

In the CRISPR-B embodiment, the pHSE401 vector is used (that is, four gRNA expression cassettes plus pHSE401). The four pieces of target sequence for BnSBE2.2 are A10-1: GGATGGCATAGTGATAACCG (SEQ ID NO: 19), A10-2: GATTCTTCTGTAACGTTGCT (SEQ ID NO: 20), C09-1: GACGACCCTACTCGAATTAA (SEQ ID NO: 21) and C09-2: GTCTTTGTAACTCTGCAACA (SEQ ID NO: 22). pHSE401 is a CRISPR/Cas9 binary vector derived from pCAMBIA. It includes, in order, (1) gRNA scaffold for insertion of target sequence (AtU6-26 promoter), (2) 2X35S promoter, (3) Zea mays codon-optimized Cas9, (4) a pea rbcS E9 terminator, (5) a Hygromycin-resistence gene as a selectable marker in plants, and (6) a marker gene, KanR (Kanamycin), a selectable marker in bacteria.

In the CRISPR-C embodiment, the pKSE401 vector is used (that is, four gRNA expression cassettes plus pKSE401). The four pieces of target sequence for BnSBE2.1 are T2: GATCGTCGTTGAAACTTGGG (SEQ ID NO: 25), T4: GAG AG AG AAG GAG AC G G C GT (SEQ ID NO: 26), T5: GTGTAGGGAAGATCTTCGCT (SEQ ID NO: 27) and T6: GCACCATCATCAACATTATC (SEQ ID NO: 28). pKSE401 is a CRISPR/Cas9 binary vector derived from pCAMBIA. It includes, in order, (1) gRNA scaffold for insertion of target sequence (AtU6-26 promoter), (2) 2X35S promoter, (3) Zea mays codon-optimized Cas9, (4) a pea rbcS E9 terminator, (5) a Kanamycin-resistence gene as a selectable marker in plants, and (6) a marker gene, KanR (Kanamycin), a selectable marker in bacteria.

These constructs are transformed into wild type *Brassica napus* plants as well as into transgenic lines overexpressing maize SBE1.

The sequence of four gRNA expression cassettes for CRISPR-A is provided as SEQ ID No: 23. The sequence is the CRISPR expression cassette representing a tandem connection of four target sequence including promoter, terminator, target sequence, as shown in FIG. 9.

The sequence of four gRNA expression cassettes for CRISPR-B is provided as SEQ ID No: 24. The sequence is the CRISPR expression cassette representing a tandem connection of four target sequence including promoter, terminator, target sequence, as shown in FIG. 9.

Methods of Transformation

Modified from the *Agrobacterium*-mediated floral-dipping method in *Arabidopsis thaliana*[66], the *Agrobacterium* solution is sprayed on immature floral buds instead of dipping. The *Agrobacterium* solution contains *Agrobacterium tumefaciens* with a final $OD_{600}$ value at 0.8, 5% sucrose, 500 microliters per litre surfactant Silwet L-77 and 6-benzylaminopurine, pH 5.8. Plants are covered immediately to maintain humidity in darkness for 1 day and then moved to normal growth conditions.

The procedure for tissue culture transformation is modified from Moloney et al.[65]. It takes approximately 90 days to obtain rooted seedlings. Seeds are first sterilized with ethanol, and then 100% Javex containing a drop of Tween 20 for 15 minutes, followed by thorough washing with sterile water. Seeds are transferred to sterile petri dishes filled with germination medium (½ MS with 1% sucrose, pH5.8), and kept in a growth room for 4-5 days. Cotyledons are collected into petri dishes and inoculated with *agrobacterium* medium (0.5 ml of *agrobacterium* suspension with 4.5 ml of inoculation medium containing MS/B5, 3% sucrose, 0.5 mg/L BA, pH5.8), kept in darkness at 25 C for 2 days, then transferred to 4 C for 3 days in darkness. Cotyledons are transferred to selection medium containing MMO, 3% sucrose, 4.5 mg/L BA, pH5.8, 0.7% agar. Transfer to fresh medium is repeated every 2-3 weeks until shoots are obtained. Shoot elongation and rooting involves incubation on shooting medium (MS/B5, 2% sucrose, 0.5 ml/L BA, 0.03 mg/L $GA_3$, 500 mg/L MES, 150 mg/L phloroglucinol, pH5.8, 0.9% phytoagar) and root induction medium (½ MS/B5, 1% sucrose, 0.5 mg/L indolebutyric acid, 500 mg/L MES, 0.8% agar, pH5.8) respectively.

Homozygous transgenic canola seeds can be generated by culturing microspores from flowering buds[68], followed by an integrated transformation system of microprojectile bombardment and *agrobacterium* infiltration[67]. Briefly, unopened flower buds are harvested, surface-sterilized with bleach and rinsed with water. Microspores are isolated by mechanical homogenization in 13% sucrose solution and then suspended in liquid Nitsch Liquid Nutrient (NLN) medium. For bombardment, microspore culture droplets are deposited onto polyester filters over solid NLN medium with sucrose and mannitol. Bombardment is performed with DNA-coated gold particles of 60 μm using a Bio-Rad PDS-1000/He biolistic particle delivery system. After that, microspores are transferred to liquid NLN medium, and 0.5 ml of a suspension of *agrobacterium* solution at $OD_{600}$ 0.016 is added. Then, the dishes are then sealed and placed at 30° C. in darkness for 10 days followed by 18 days in a shaker in the dark. The mature cotyledonary embryos are transferred to solid MS/B5 medium, placed in a 4° C. chamber for 10 days. Plants are then moved to 25° C. in light for germination for about 30 days and then haploid plantlets are transplanted to soil and placed in the greenhouse. When plants begin to flower, the chromosome number of haploids is doubled with 0.34% colchicine solution.

Example 4

Maize SBE1 is expressed in *Brassica napus* using the methods of Example 2. Endogenous SBE2.1 and SBE2.2 are then knocked out in the transformed *Brassica napus* plant using the methods and CRISPR constructs of Example 3. The knockout is assayed for an increase in biomass and oil production in comparison to wild type *Brassica napus*.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety.

REFERENCES

1. Smith, A. M. Prospects for increasing starch and sucrose yields for bioethanol production. *Plant J.* 54, 546-558 (2008).
2. Dyer, J. M., Stymne, S., Green, A. G. & Carlsson, A. S. High-value oils from plants. *Plant J.* 54, 640-655 (2008).
3. Durrett, T., Benning, C., & Ohlrogge, J. Plant triacylglycerols as feedstocks for the production of biofuels. *Plant J.* 54, 593-607 (2008).
4. Parry, M. A. J. & Hawkesford, M. J. Food security: increasing yield and improving resource efficiency. *Proceedings of the Nutrition Society* 69, 592-600 (2010).

5. Long, S. P., Zhu, X. G., Naidu, L., and Ort, D. Can improvement in photosynthesis increase crop yields? *Plant Cell Environment* 29, 315-330 (2006).
6. Raines, C. A. Transgenic approaches to manipulate the environmental responses of the $C_3$ carbon fixation cycle. *Plant Cell Environment* 29, 331-339 (2006).
7. Sinclair, T. R., Purcell, L. C., and Sneller, C. H. Crop transformation and the challenge top increase yield potential. *Trends in Plant Science* 9, 70-75 (2004).
8. Lemaux, P. G. Genetically engineered plants and food: a scientist's analysis of the issues (part I) *Annual Review of Plant Biology* 59, 771-812 (2008).
9. Asch, F., and Wopereis, M. C. S. Responses of field-grown irrigated rice cultivars to varying levels of floodwater salinity in a semi-arid environment. *Field Crops Research* 70, 127-137(2001).
10. Andersen, M. N., Asch, F., Wu, Y., Jensen, C. R., Naested, H., Mogensen, V. O., and Koch, K. E. Soluble invertase expression is an early target of drought stress during the critical, abortion-sensitive phase of young ovary development in maize. *Plant Physiology* 130, 591-604 (2002).
11. Sun, K., Hunt, K. & Hauser, B. A. Ovule abortion in *Arabidopsis* triggered by stress. *Plant Physiol* 135, 2358-2367 (2004)
12. Yu, T.-S., Lue, W.-L., Wang, S.-M., and Chen, J. Mutations of *Arabidopsis* plastid phosphoglucose isomerase affects leaf starch synthesis and floral initiation. *Plant Physiology* 123, 319-325 (2000).
13. Cernac, A. & Benning, C. WRINKLED1 encodes an AP2/EREB domain protein involved in the control of storage compound biosynthesis in *Arabidopsis*. *Plant J.* 40, 575-585 (2004).
14. Shen, B., Allen, W. B., Zheng, P., Li, C., Glassman, K., Ranch, J., Nubel, D., & Tarczynski, M. C. Expression of ZmLEC1 and ZmWRI1 increases seed oil production in maize. *Plant Physiol.* 153, 980-987 (2010).
15. Jako, C., Kumar, A., Wei, Y., Zou, J., Barton D. L., Giblin, E. M., Covello, P. S., & Taylor, D. C. Seed-specific over-expressio of an *Arabidopsis* cDNA encoding a diacylglycerol acyltransferase enhances seed oil content and seed weight. *Plant Physiol.* 126, 861-874 (2001).
16. Fan, J., Yan, C., Zhang, X., & Xu, C. Dual role for phospholipid:diacylglycerol acyltransferase: enhancing fatty acid synthesis and diverting fatty acids from membrane lipids to triacylglycerol in *Arabidopsis* leaves. *Plant Cell* 25, 3506-3518 (2013).
17. Kelly, A. A., Shaw, E., Powers, S. J., Kurup, S., & Eastmond, P. J. Suppression of the SUGAR-DEPENDENT1 triacylglycerol lipase family during seed development enhances oil yield in oilseed rape (*Brassica napus* L.). *Plant Biotechnol. J.* 11, 355-361 (2013).
18. Winichayakul, S., Scott, R. W., Roldan, M., Hatier, J. H., Livingston, S., Cookson, R., Curran, A. C., & Roberts, N. J. In vivo packaging of triacylglycerols enhances *Arabidopsis* leaf biomass and energy density. *Plant Physiol.* 162, 626-639 (2013).
19. Vanhercke, T. et al. Metabolic engineering of biomass for high energy density: oilseed-like triacylglycerol yields from plant leaves. *Plant biotechnology journal* 12, 231-239 (2014).
20. Vanhercke, T., El Tahchy, A., Shrestha, P., Zhou, X. R., Singh, S. P., & Petrie, J. R. synergistic effect of WRI1 and DGAT1 coexpression on triacylglycerol biosynthesis in plants. *FEBS Lett.* 587, 364-369 (2013).
21. van Erp, H., Kelly, A. A., Menard, G., & Eastmond, P. J. Multigene engineering of triacylglycerol metabolism boosts seed oil content in *Arabidopsis*. *Plant Physiol.* 165, 30-36 (2014).
22. Stark, D. M., Timmerman, K. P., Barry, G. F., Preiss, J. & Kishore, G. M. Regulation of the amount of starch in plant tissues by ADP glucose pyrophosphorylase. *Science* 258, 287-292 (1992).
23. Sweetlove, L. J., Burrell, M. M. & ap Rees, T. Starch metabolism in tubers of transgenic potato (Solanum tuberosum) with increased ADPglucose pyrophosphorylase. *Biochem. J.* 320, 493-498 (1996).
24. Giroux, M. J. et al. A single mutation that increases maize seed weight. *Proceedings of the National Academy of Sciences* 93, 5824-5829 (1996).
25. Patrick, J. W., & Colyvas, K. (2014). Crop yield components—photoassimilate supply—or utilisation limited organ development? *Functional Plant Biology* 41, 893-913.
26. Hadrich, N. et al. Mutagenesis of cysteine 81 prevents dimerization of the APS1 subunit of ADP-glucose pyrophosphorylase and alters diurnal starch turnover in *Arabidopsis thaliana* leaves. *The Plant journal: for cell and molecular biology* 70, 231-242 (2012).
27. Tuncel A., and Okita, T. W. Improving starch yield in cereals by overexpression of ADPglucose pyrophosphorylase: expectations and unanticipated outcomes. *Plant Science* 211, 52-60 (2013)
28. Smidansky, E. D., Martin, J. M., Hannah, L. C., Fischer, A. M., & Giroux, M. J. Seed yield and plant biomass increases in rice are conferred by deregulation of endosperm ADP-glucose pyrophosphorylase. *Planta* 216, 656-664 (2003).
29. Smidansky, E. D., Clancy, M., Meyer, F. D., Lanning, S. P., Blake, N. K., Talbert, L. E., & Giroux, M. J. Enhanced ADP-gluucose pyrophosphorylase activity in wheat endosperm increases seed yield. *Proc. Nat. Acad. Sci. USA* 99, 1724-1729 (2002).
30. Hannah, L. C., Futch, B., Bing, J., Shaw, J. R., Boehlein, S., Stewart, J. D., Beiriger, R., Georgelis, N., & Greene, T. A shrunken-2 transgene increases maize yield by acting in maternal tissues to increase the frequency of seed development. *Plant Cell* 24, 2352-2363 (2012).
31. Ball, S., Colleoni, C., Cenci, U., Raj, J. N. & Tirtiaux, C. The evolution of glycogen and starch metabolism in eukaryotes gives molecular clues to understand the establishment of plastid endosymbiosis. *J Exp Bot* 62, 1775-1801 (2011)
32. Morell, M. K., Blennow, A., Kosar-Hashemi, B., and Samuel, M. S. Differential expression and properties of starch branching enzyme isoforms in developing wheat endosperm. *Plant Physiology* 113, 201-208 (1997).
33. Tomlinson, K., and Denyer, K. Starch synthesis in cereal grains. *Advances in Botanical Research* 40, 1-71(2003)
34. Dumez, S., Wattebled, F., Dauvillée, D., Delvallé, D., Planchot, V., Ball, S. G., and D'Hulst, C. Mutants of *Arabidopsis* lacking starch branching enzyme II substitute plastidial starch synthesis by cytoplasmic maltose accumulation. *Plant Cell* 18, 2694-2709 (2006).
35. Androitis, V. M., Pike, M. J., Kular, B., Rawsthorne, S., and Smith, A. M. Starch turnover in developing oilseed embryos. *New Phytologist* 187, 791-804 (2010).
36. Guan, H.-P., and Preiss, J. Differentiation of the properties of the branching isozymes from maize (*Zea mays*). *Plant Physiology* 102, 1269-1273 (1993).
37. Xia, H., Yandeau-Nelson, M., Thompson, D. B., and Guiltinan, M. J. Deficiency of maize starch-branching 37. enzyme I results in altered fine structure, decreased digestibility and reduced coleoptile growth during germination. *BMC Plant Biology* 11, 95 (2011).
38. Yandeau-Nelson, M. D., Laurens, L., Shi, Z., Xia, H., Smith, A. M., and Guiltinan, M. J. Starch-branching enzyme IIa is required for proper diurnal cycling of starch in leaves of maize. *Plant Physiology* 156, 479-490 (2011).
39. Schwall, G. P. et al. Production of very-high-amylose potato starch by inhibition of SBE A and B. *Nat Biotech* 18, 551-554 (2000).
40. Smith, A. M. Starch in the *Arabidopsis* plant. Starch/Stärke 64, 421-434 (2012).
41. Sun, K., Hunt, K. & Hauser, B. A. Ovule abortion in *Arabidopsis* triggered by stress. *Plant Physiol* 135, 2358-2367 (2004).
42. Schussler, J. R. & Westgate, M. E. Assimilate Flux Determines Kernel Set at Low Water Potential in Maize. *Crop Sci.* 35, 1074-1080 (1995).
43. Smidansky, E. D., Meyer, F. D., Blakeslee, B., Weglarz, T. E., Greene, T. W., Giroux, M. J. Expression of a modified ADP-glucose pyrophosphorylase large subunit in wheat seeds stimulates photosynthesis and carbon metabolism. *Planta* 225, 965-976 (2007).
44. Ral, J. P. et al. Down-regulation of Glucan, Water-Dikinase activity in wheat endosperm increases vegetative biomass and yield. *Plant biotechnology journal* 10, 871-882 (2012).
45. Graf, A. and Smith, A. M. Starch and the clock: the dark side of plant productivity. *Trends in Plant Science* 16, 169-175 (2011).
46. Sulpice, R. et al. Starch as a major integrator in the regulation of plant growth. *Proc Natl Acad Sci USA* 106, 10348-10353 (2009).
48. Weigel, D. & Glazebrook, J. Cultivation of *Arabidopsis*. *Arabidopsis*: A Laboratory Manual., 354 (2002).
49. Zhang, X., Henriques, R., Lin, S. S., Niu, Q. W. & Chua, N. H. *Agrobacterium*-mediated transformation of *Arabidopsis thaliana* using the floral dip method. *Nature protocols* 1, 641-646 (2006).
50. Delatte, T., Trevisan, M., Parker, M. L. & Zeeman, S. C. *Arabidopsis* mutants Atisa1 and Atisa2 have identical phenotypes and lack the same multimeric isoamylase, which influences the branch point distribution of amylopectin during starch synthesis. *The Plant Journal: for cell and molecular biology* 41, 815-830 (2005).
51. Xu, W. et al. An improved agar-plate method for studying root growth and response of *Arabidopsis thaliana*. *Scientific reports* 3, 1273 (2013).
52. Abramoff, M. D. M., Paulo J.; Ram, Sunanda J. Image processing with ImageJ. *Biophotonics international* 11 (2004).
53. James, C. N. et al. Disruption of the *Arabidopsis* CGI-58 homologue produces Chanarin-Dorfman-like lipid droplet accumulation in plants. *Proceedings of the National Academy of Sciences* 107, 17833-17838 (2010).
54. Smith, A. M. & Zeeman, S. C. Quantification of starch in plant tissues. *Nature protocols* 1, 1342-1345 (2006).
55. Bertoft, E., Piyachomkwan, K., Chatakanonda, P. & Sriroth, K. Internal unit chain composition in amylopectins. *Carbohydrate Polymers* 74, 527-543 (2008).
56. Nitschke, F. et al. Hyperphosphorylation of glucosyl C6 carbons and altered structure of glycogen in the neurodegenerative epilepsy Lafora disease. *Cell metabolism* 17, 756-767 (2013).
57. Wilson, J. D., Bechtel, D. B., Todd, T. C. & Seib, P. A. Measurement of wheat starch granule size distribution using image analysis and laser diffraction technology. *Cereal chemistry.* 83, 259-268 (2006).
58. Liu, F. et al. The amylose extender mutant of maize conditions novel protein-protein interactions between starch biosynthetic enzymes in amyloplasts. *J Exp Bot* 60, 4423-4440 (2009).
59. Guevara, D. R., El-Kereamy, A., Yaish, M. W., Mei-Bi, Y. & Rothstein, S. J. Functional characterization of the rice UDP-glucose 4-epimerase 1, OsUGE1: a potential role in cell wall carbohydrate partitioning during limiting nitrogen conditions. *PloS one* 9, e96158 (2014).
60. Lilly, S. T., Drummond, R. S. M., Pearson, M. N. & MacDiarmid, R. M. Identification and Validation of Reference Genes for Normalization of Transcripts from Virus-*Infected Arabidopsis thaliana*. *Molecular Plant-Microbe Interactions* 24, 294-304 (2010).
61. Livak, K. J. and Schmittgen, T. D. Analysis of Relative Gene Expression Data Using Real-Time Quantitative PCR and the 2-ΔΔCT Method. *Methods* 25, 402-408 (2001).
62. Facon, M. et al. Distinct functional properties of iso-amylase-type starch debranching enzymes in monocot and dicot leaves. *Plant Physiol* (2013).
63. Rensing, K. H., Samuels, A. L. & Savidge, R. A. Ultrastructure of vascular cambial cell cytokinesis in pine seedlings preserved by cryofixation and substitution. *Protoplasma* 220, 39-49 (2002).
64. Xing et al. A CRISPR/Cas9 toolkit for multiplex genome editing in plants. *BMC Plant Biol.* 14:327. doi: 10.1186/s12870-014-0327-y (2014).
65. Moloney, M. M., Walker, J. M. and Sharma, K. K. High efficiency transformation of *Brassica napus* using *Agrobacterium* vectors. *Plant Cell Rep.* 8:238-242. (1989).
66. Zhang, X. et al. *Agrobacterium*-mediated transformation of *Arabidopsis thaliana* using the floral dip method. *Nature Protocols* 1: 641-646. (2006).
67. Abdollahi M. R., An efficient method for transformation of pre-androgenic, isolated *Brassica napus* microspores involving microprojectile bombardment and *Agrobacterium*-mediated transformation. *Acta Physiologiae Plantarum.* 31:1313 (2009).
68. Burbulis N. and Kott L. S. Application of doubled haploid technology in breeding of *Brassica napus*. In book: From plant genomics to plant biotechnology, Chapter: 10, Publisher: Woodhead Publishing Limited, pp.183-203 (2013).
69. Corbesier, L., Lejeune, P., and Bernier, G. (1998). The role of carbohydrates in the induction of flowering in *Arabidopsis thaliana*: comparison between the wild type and a starchless mutant. Planta 206: 131-137.
70. Eveland, A. L., and Jackson, D. P. (2012). Sugars, signalling and plant development. Journal of Experimental Botany 63: 3367-3377.

The invention claimed is:

1. A transgenic plant produced using a method comprising:
   a. contacting a plant cell with a nucleic acid molecule encoding an exogenous starch-branching enzyme selected from starch-branching enzyme 1 (SBEI) and starch-branching enzyme 2b (SBEIIb) to obtain a transformed plant cell,
   b. expressing the nucleic acid molecule in the transformed plant cell, and
   c. producing a plant from the transformed plant cell,
   wherein the nucleic acid molecule is from a cereal plant and wherein the plant is a dicotyledon,
   wherein the plant has increased biomass, seed production and/or oil production compared to a wild-type plant not transformed with the nucleic acid molecule,
   wherein the nucleic acid molecule comprises a nucleic acid sequence that has at least 80% sequence identity with a nucleic acid sequence selected from SEQ ID NO: 1 or 3, and
   wherein the cereal plant is maize, wheat, barley, sorghum, oat, rye, millet, triticale or rice.

2. A transgenic seed of the plant of claim 1.

3. A transgenic plant cell of the plant of claim 1.

4. A transformed plant cell, plant or plant part expressing at least one nucleic acid molecule encoding an exogenous starch-branching enzyme selected from starch-branching enzyme 1 (SBEI) and starch-branching enzyme 2b (SBEIIb), wherein the nucleic acid molecule is from a cereal plant and the transformed plant cell, plant or plant part is a dicotyledon and wherein said transformed plant or plant part or a plant or plant part obtained from said transformed plant cell has increased biomass, seed production and/or oil production compared to a wild-type plant or plant part not transformed with the nucleic acid molecule,
   wherein the nucleic acid molecule comprises a nucleic acid sequence that has at least 80% sequence identity with a nucleic acid sequence selected from SEQ ID NO: 1 or 3, and
   wherein the cereal plant is maize, wheat, barley, sorghum, oat, rye, millet, triticale or rice.

5. The transformed plant cell, plant or plant part of claim 4, wherein the activity or expression of at least one endogenous starch-branching enzyme in the transformed plant cell, plant or plant part is reduced or eliminated independently from expression of the nucleic acid molecule.

6. The transformed plant cell, plant or plant part of claim 4, wherein the transformed plant cell, plant or plant part is an oil-seed crop.

7. The transformed plant cell, plant or plant part of claim 4 expressing a first nucleic acid molecule encoding a first exogenous starch-branching enzyme and a second nucleic acid molecule encoding a second exogenous starch-branching enzyme.

8. The transformed plant cell, plant or plant part of claim 7, wherein the first nucleic acid molecule comprises a nucleic acid sequence that has at least 80% sequence identity with SEQ ID NO: 1, and the second nucleic acid molecule comprises a nucleic acid sequence that has at least 80% sequence identity with SEQ ID NO: 3.

9. The transformed plant cell, plant or plant part of claim 6, wherein the oil-seed crop is canola, camelina, cotton, flaxseed, mustard, rapeseed, soybean, sunflower seed or palm.

10. The transgenic plant of claim 1, wherein the method further comprises the step of reducing the activity or expression of at least one endogenous starch- branching enzyme in the plant cell.

* * * * *